(12) United States Patent  
Fischer

(10) Patent No.: US 7,794,736 B2  
(45) Date of Patent: Sep. 14, 2010

(54) **CANINE *LEISHMANIA* VACCINE**

(75) Inventor: Laurent Bernard Fischer, Sainte Foy les Lyon (FR)

(73) Assignee: Merial Limited, Duluth, GA (US)

( * ) Notice: Subject to any disclaimer, the term of this patent is extended or adjusted under 35 U.S.C. 154(b) by 111 days.

(21) Appl. No.: 11/942,457

(22) Filed: Nov. 19, 2007

(65) Prior Publication Data

US 2008/0241193 A1 Oct. 2, 2008

Related U.S. Application Data

(60) Provisional application No. 60/866,848, filed on Nov. 21, 2006.

(51) Int. Cl.  
*A61K 39/00* (2006.01)

(52) U.S. Cl. .................................. 424/269.1

(58) Field of Classification Search ........................ None  
See application file for complete search history.

(56) References Cited

U.S. PATENT DOCUMENTS

| | | | |
|---|---|---|---|
| 7,598,364 B2 * | 10/2009 | Fisher | 536/23.1 |
| 2006/0194753 A1 * | 8/2006 | Wittig et al. | 514/44 |
| 2008/0145385 A1 * | 6/2008 | Basu et al. | 424/269.1 |

FOREIGN PATENT DOCUMENTS

WO  WO 2005/039633 A  5/2005

OTHER PUBLICATIONS

Greenspan et al. (Nature Biotechnology 7: 936-937, 1999).*  
Campbell (Monoclonal antibody Technology pp. 3-5, 1984).*  
Basu R, et al., "Kinetoplastid membrane protein-11 DNA vaccination induces complete protection against both pentavalent antimonial-sensitive and resistant strains of *Leishmania donovani* that correlates with inducible nitric oxide synthase activity and IL-4 Generation: Evidence for Mixed Th1- and Th2-like responses in Visceral Leishmaniasis", Journal of Immunology (2005), vol. 174, No. 11, pp. 7160-7171.  
Ivory C, et al., "DNA vaccines: designing strategies against parasitic infections", Genetic Vaccines and Therapy, Biomed Central (2004) Vo. 2, No. 1, p. 17.  
Woodland, D L, "Jump-starting the immune system: prime-boosting comes of age", Trends in Immunology (2004) vol. 25, No. 2, pp. 98-104.  
Doria-Rose, N A, et al., "DNA vaccine strategies: candidates for immune modulation and immunization regimens", Methods: A companion to Methods in Enzymology (2003) vol. 31, No. 3, pp. 207-216.  
Liljeqvist S, et al., "Production of recombinant subunit vaccines: protein immunogens, live delivery systems and nucleic acid vaccines" Journal of Biotechnology (1999) vol. 73, No. 1 pp. 1-33.  
Perez-Jimenez, et al., "MVA-LACK as a safe and efficient vector for vaccination against leishmaniasis", Microbes and Infection (2006) vol. 8, No. 3 pp. 810-822.

(Continued)

*Primary Examiner*—Robert B Mondesi  
*Assistant Examiner*—Nina A Archie  
(74) *Attorney, Agent, or Firm*—Judy Jarecki-Black; Ruoying Chen; Merial Limited

(57) ABSTRACT

The present invention provides vectors that contain and express in vivo *Leishmania* KMP11 or an epitope thereof that elicits an immune response in a dog against *Leishmania*, compositions comprising said vectors, methods of vaccination against *Leishmania*, and kits for use with such methods and compositions.

13 Claims, 10 Drawing Sheets

OTHER PUBLICATIONS

Oliveira, et al., "From transcriptome to immunome: Identification of DTH inducing proteins from a *Phlebotomus ariasi* salivary gland cDNA library", Vaccine, Butterworth Scientific, (2006) vol. 24, No. 3 pp. 374-390.

Planelles L, et al., "DNA immunization with *Trypanosoma cruzi* HSP70 Fused to the KMP11 Protein Elicits a Cytotoxic and Humoral Immune Response against the Antigen and Leads to Protection", Infection and Immunity (2001) vol. 69, No. 10 pp. 6558-6563.

* cited by examiner

| Lane | Samples | Restriction fragments containing DNA complementary to the *KMP-11*-specific probe are indicated in red. |
|---|---|---|
| 1. | 1 kb Plus DNA Ladder | |
| 2. | vCP2350.1.1.5*Bgl* II | |
| 3. | ALVAC*Bgl* II | |
| 4. | vCP2350.1.1.5*Hin*d III | vCP2350.1.1.5*Bgl* II: 1074 bp |
| 5. | ALVAC*Hin*d III | vCP2350.1.1.5*Hin*d III: 10749 bp |
| 6. | vCP2350.1.1.5*Pst* I | vCP2350.1.1.5*Pst* I: 17939 bp |
| 7. | ALVAC*Pst* I | |
| 8. | 1 kb DNA Extension Ladder | Note that each of the above bands is comprised by equivalent fragments derived from both ITRs. |

| Lane | Samples | Restriction fragments containing DNA complementary to the *KMP-11*-specific probe |
|---|---|---|
| 1. | 1 kb Plus DNA Ladder | |
| 2. | vCP2350.1.1.5:*Bgl* II | |
| 3. | ALVAC:*Bgl* II | |
| 4. | vCP2350.1.1.5:*Hind* III | vCP2350.1.1.5*Bgl* II: 1074 bp |
| 5. | ALVAC:*Hind* III | vCP2350.1.1.5*Hind* III: 10749 bp |
| 6. | vCP2350.1.1.5:*Pst* I | vCP2350.1.1.5*Pst* I: 17939 bp |
| 7. | ALVAC:*Pst* I | |
| 8. | 1 kb DNA Extension Ladder | Note that each of the above bands is comprised by equivalent fragments derived from both ITRs. |

| Lane | Samples |
|---|---|
| 1. | 1 kb Plus DNA Ladder |
| 2. | vCP2350.1.1.5:*Bgl* II |
| 3. | ALVAC:*Bgl* II |
| 4. | vCP2350.1.1.5:*Hin*d III |
| 5. | ALVAC:*Hin*d III |
| 6. | vCP2350.1.1.5:*Pst* I |
| 7. | ALVAC:*Pst* I |
| 8. | 1 kb DNA Extension Ladder |

Restriction fragments containing DNA complementary to the *KMP-11*-specific probe vCP2350.1.1.5:*Bgl* II: 1074 bp
vCP2350.1.1.5:*Hin*d III: 10749 bp
vCP2350.1.1.5:*Pst* I: 17939 bp Note that each of the above bands is comprised by equivalent fragments derived from both ITRs.

CANINE *LEISHMANIA* VACCINE

INCORPORATION BY REFERENCE

This application claims benefit of U.S. provisional patent application Ser. No. 60/866,848 filed Nov. 21, 2006.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to the field of vaccine against Leishmaniasis, specifically against canine Leishmaniasis.

BACKGROUND ART

Leishmaniasis is a major and severe parasitic disease of humans, canids (dogs, wolves, foxes, coyotes, jackals), and felids (lions, tigers, domestic cats, wild cats, other big cats, and other felines including cheetahs and lynx).

The agent of leishmaniasis is a protozoan parasite and belongs to the *leishmania donovani* complex. This parasite is widely distributed in temperate and subtropical countries of Southern Europe, Africa, Asia, South America and Central America (Desjeux P., Trans. R. Soc. Trop. Med. Hyg., 2001, 95: 239-43). *Leishmania donovani infantum* (*L. infantum*) is responsible for the feline and canine disease in Southern Europe, Africa, and Asia. In South America and Central America, the agent is *Leishmania donovani chagasi* (*L. chagasi*), which is closely related to *L. infantum*. In humans, the agent is *Leishmania donovani donovani* (*L. donovani*), which is closely related to *L. infantum* and *L. chagasi*.

The parasite is transmitted to humans, felids and canids by sand flies, which species vary depending on the geographic location. *Phlebotomus ariasi* (*P. ariasi*) and *Phlebotomus perniciosus* (*P. perniciosus*) are the carriers most common in Southern Europe, Africa, and Asia, whereas *Lutzomyia longipalpis* (*L. longipalpis*) is most common in Southern and Central America.

The domestic reservoir of Leishmaniasis are dogs, which may suffer from a severe disease characterized by chronic evolution of viscero-cutaneous signs occurring in less than 50% of infected animals (Lanotte G. et al., Ann. Parasitol. Hum. Comp., 1979, 54: 277-95). On the other hand, both asymptomatic and symptomatic dogs with detectable antibodies can be infectious to phlebotomine vectors (Molina R. et al., Trans. R. Soc. Trop. Med. Hyg., 1994, 88: 491-3; Courtenay O. et al., J. Infect. Dis., 2002, 186: 1314-20). Cats can be carriers of the protozoan parasites and are considered as secondary potential reservoirs.

These parasites cause visceral leishmaniasis and/or cutaneous leishmaniasis. Visceral leishmaniasis results in clinical symptoms like fever, cachexia, hepatosplenomegaly (enlargement of the liver and spleen), and blood cytopenia. Cutaneous leishmaniasis occurs in varying presentations, from the self-limited and even self-healing cutaneous forms to fatal systemic disease. Lesions of cutaneous leishmaniasis may occur anywhere on the body but the most common sites are those which are exposed to the environment and are therefore more susceptible to bites from the sand flies. The initial papule rapidly gives rise to an ulcer. Systemic leishmaniasis is rare but is invariably fatal if not treated promptly. Systemic leishmaniasis affects the internal body organs, specifically the spleen and the liver.

In canines, the disease is associated with cutaneous symptoms or with visceral symptoms or both cutaneous and visceral symptoms, and is lethal in the absence of therapy.

Numerous treatments have been described but none is fully satisfactory due to toxicity of the treatment itself or a tendancy for the animal to relapse.

Mass detection of seropositive dogs followed by culling and/or drug treatment, or the mass application of deltamethrin-impregnated collars, was shown to have an impact in reducing human and canine Leishmaniasis prevalence in endemic areas of Southern Europe, Africa, and Asia (Maroli M. et al., Med. Vet. Entomol., 2001, 15: 358-63; Mazloumi Gavgani A. S. et al., Lancet, 2002, 360: 374-9), although the efficacy of eliminating seropositive canines has been debated (Dietze R. et al., Clin. Infect. Dis., 1997, 25: 1240-2; Moreira Jr. E. D. et al., Vet. Parasitol., 2004, 122: 245-52). These control measures are either consideur unacceptable, expensive or not effective (Gradoni L. et al., Vaccine, 2005, 23: 5245-51).

Mathematical models used to compare the effectiveness of various tools for controlling Leishmaniasis suggest that a canine vaccine may be the most practical and effective method (Dye C., Am. J. Trop. Med. Hyg., 1996, 55: 125-30). Therefore, the development of vaccines able to protect canids from leishmaniasis and/or to prevent disease progression in infected animals, is highly desirable for the implementation of Leishmaniasis control programs as well for the veterinary community (Gradoni L. et al., Vaccine, 2005, 23: 5245-51).

The state of the art is best summarized in US patent application US-A-2006/0194753. This document describes a vaccine containing a DNA expression vector encoding *L. infantum* KMP11 (kinetoplastid membrane protein 11) protein. However, the experimental results on mice (as shown in FIG. 1 of 2006/0194753) showed that mice vaccinated with pMCV1.4 plasmids expressing KMP11 had worse results than the control mice as to the presence of lesions within 8 weeks after challenge infection (lesion scores of about 3.2 and about 1.6 for vaccinated and control mice, respectively). Furthermore, experiments on dogs in FIG. 2 of 2006/0194753 show that after administration of a mixture of one recombinant pMOK plasmid expressing *L. infantum* p36 antigen and three recombinant pMCV1.4 plasmids expressing *L. infantum* TSA (thiol-specific antioxidant protein), *L. infantum* gp63 and *L. infantum* KMP11 antigens, no antibodies were detectable. There was no clear difference between the results of the vaccinated group and those of the control group. After challenge infection with $10^{7.7}$ *L. infantum* promastigotes, the number of infected dogs in the vaccinated group showed only a slight difference to the control group.

Basu et al. (Basu R. et al., J. Immunol., 2005, 174: 7160-71) described an experiment using golden hamsters immunized with KMP11 containing pCMV-LIC mammalian expression vector versus control animals immunized with a blank vector construct not harboring KMP11 (pCMV-LIC). Animals of both groups received two intramuscular administrations to the hind leg thigh muscle (using a 28-guage needle), given 8 days apart, of 100 µg of plasmids dissolved in saline. On day 15, a lethal parasite challenge was done with either of two strains, *L donovani* AG83 or *L. donovani* GE1F8R. All of the vaccinated hamsters immunized with KMP11 DNA survived the lethal challenge of AG83 and GE1F8R and remained healthy until the termination of the experiment at 8 months postinfection, whereas all non-immunized and blank vector-immunized hamsters succumbed to virulent *L. donovani* challenge within 6 months.

Currently, no vaccine is available for *Leishmania*-susceptible subjects, including for canids.

SUMMARY OF THE INVENTION

Accordingly, the present invention relates to an innovative vaccine strategy, which is based on *Leishmania* KMP11 (kinetoplastid membrane protein 11) antigen in order to prevent diffusion and implantation of the parasite into internal organs.

It is therefore an object of this invention to provide a vaccine capable of protecting subjects (i.e., canids, felids, and humans) from leishmaniasis and/or to prevent disease progression in infected subjects.

It is also an object of the present invention to provide methods of using such vaccines in order to protect canids from leishmaniasis and/or to prevent disease progression in infected canids.

It is also an object of the present invention to provide methods of using such vaccines in order to protect felids from leishmaniasis and/or to prevent disease progression in infected felids.

It is also an object of the present invention to provide methods of using such vaccines in order to protect humans from leishmaniasis and/or to prevent disease progression in infected humans.

It is therefore additionally an object of this invention to provide in vivo expression vectors encoding *Leishmania* KMP11 antigen or immunogen or an epitope thereof for such vaccines and/or such methods of use.

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF DRAWINGS

The following detailed description, given by way of example, and which is not intended to limit the invention to specific embodiments described, may be understood in conjunction with the accompanying figures, incorporated herein by reference, in which.

Figure 1:
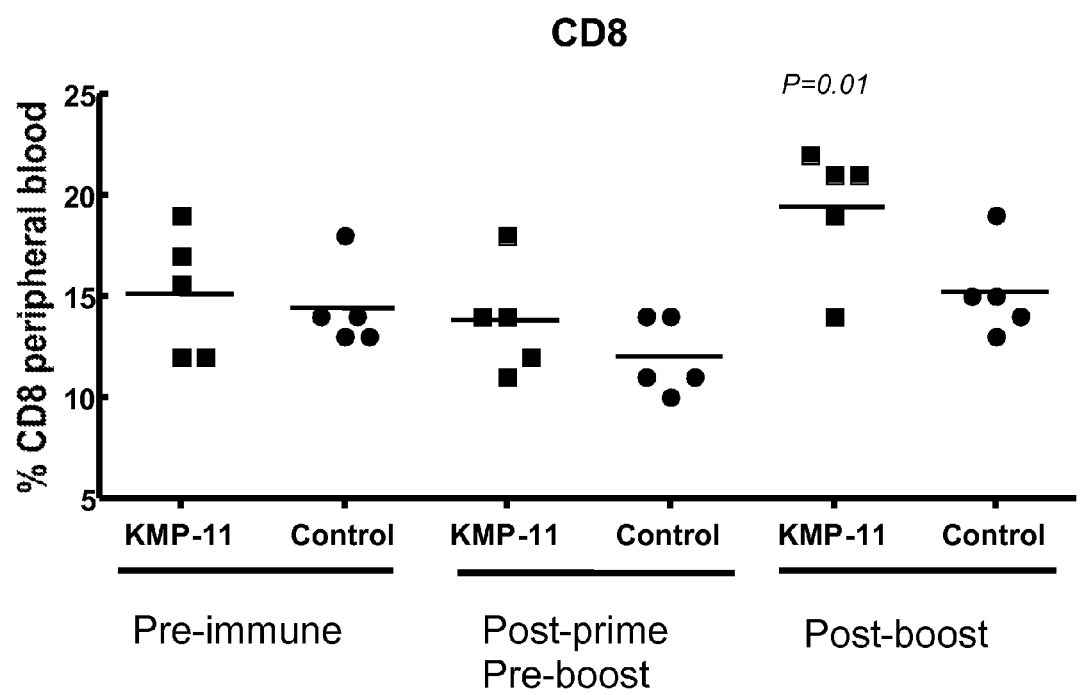
FIG. 1 shows the frequency of CD8 before vaccination, between an initial vaccination and a subsequent boost vaccination, and after boost-vaccination; expressed in percentage of CD8 cells present in the peripheral blood.

The sequences SEQ ID No1 and SEQ ID No2 show the nucleic acid sequence of *L. infantum* KMP11 of the strain of used in the examples and the amino acid sequence of the protein encoded by this nucleic acid sequence, respectively.

The sequence SEQ ID No3 shows the codon-optimized nucleic acid sequence encoding the KMP11 protein of *L. infantum* as presented in NCBI GenBANK database accession number CAA64883 and in SEQ ID No4.

The sequence SEQ ID No5 shows the nucleic acid sequence of one strand of the plasmid pVR1020KMP11.

The sequence SEQ ID No6 shows the nucleic acid sequence of one strand of the ALVAC donor plasmid pJSY1992.1.

DETAILED DESCRIPTION

In one aspect, the present invention relates to a vaccine strategy, which is based on a prime-boost administration regimen, where the primo-administration and the boost administration(s) utilize a composition comprising a pharmaceutically or veterinary acceptable excipient, diluent or vehicle and an in vivo expression vector comprising a polynucleotide sequence, that contains and expresses the *Leishmania* antigen KMP11 or immunogen or epitopes thereof, as described herein.

*Leishmania* KMP11 antigens are derived from, for example, *L. infantum* or *L. chagasi*. KMP11 is a highly conserved surface membrane protein present in all members of the family Kinetoplastidae, and is differentially expressed both in amastigote and promastigote forms of *Leishmania* (Jardim A. et al., Biochem. J., 1995, 305: 315-20; Jardim A. et al., Biochem. J., 1995, 305: 307-13; Berberich C. et al., Biochim. Biophys. Acta, 1998, 1442: 230-7). The nucleic acid sequence of the gene and the amino acid sequence of the protein KMP11 of *Leishmania* are available in publicly accessible databases, notably as *L. infantum* in the GenBank database under the accession numbers X95627 and X95626. The nucleic acid sequence of *L. donovani* is also available from the GenBank database, notably under the accession number S77039.

The present invention relates to the use of in vivo expression vectors in a prime-boost administration regimen, comprising a primo-administration of a vaccine comprising, in a pharmaceutically acceptable vehicle, diluent or excipient, an in vivo expression vector containing a polynucleotide sequence for expressing, in vivo, *Leishmania* KMP11 polypeptide, antigen, epitope or immunogen, followed by a boost administration of a vaccine comprising, in a pharmaceutically acceptable vehicle or excipient, an in vivo expression vector containing a polynucleotide sequence for expressing, in vivo, *Leishmania* KMP11 antigen, epitope or immunogen to protect canids, felids and humans from leishmaniasis and/or to prevent disease progression in infected canids, felids and humans.

By definition, a prime-boost regimen comprises at least one primo-administration and at least one boost administration using at least one common polypeptide, antigen, epitope or immunogen. The vaccine used in primo-administration can different in nature from those used as a later booster vaccine. The primo-administration may comprise one or more administrations. Similarly, the boost administration may comprise one or more administrations.

In a further aspect, the present invention relates to a vaccine composition comprising a pharmaceutically or veterinarily acceptable excipient, diluent or vehicle and an in vivo expression vector comprising a polynucleotide sequence, which contain and express the *Leishmania* antigen KMP11 or immunogen or epitopes thereof, as described below.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a protein, a polypeptide, a peptide, an epitope, a hapten, or any combination thereof. Alternately, the immunogen or antigen may comprise a toxin or antitoxin.

The term "immunogenic protein or peptide" as used herein also refers includes peptides and polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. The term epitope relates to a protein site able to induce an immune reaction of the humoral type (B cells) and/or cellular type (T cells).

The term "immunogenic protein or peptide" further contemplates deletions, additions and substitutions to the sequence, so long as the polypeptide functions to produce an immunological response as defined herein. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

The terms "immunogenic" protein or polypeptide as used herein also refers to an amino acid sequence which elicits an immunological response as described above. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708, 871; Geysen et al., 1984; Geysen et al., 1986, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of *T. parva* are fully described in the PCT Application Serial No. PCT/US2004/022605 incorporated herein by reference in its entirety.

Synthetic antigens are also included within the definition, for example, polyepitopes, flanking epitopes, and other recombinant or synthetically derived antigens. See, e.g., Bergmann et al., 1993; Bergmann et al., 1996; Suhrbier, 1997; Gardner et al., 1998. Immunogenic fragments, for purposes of the present invention, will usually include at least about 3 amino acids, preferably at least about 5 amino acids, more preferably at least about 10-15 amino acids, and most preferably about 15-25 amino acids or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it comprises or consists essentially of or consists of nucleotides to encode an epitope or antigenic determinant of an influenza protein or polyprotein. A polynucleotide encoding a fragment of the total protein or polyprotein, more advantageously, comprises or consists essentially of or consists of a minimum of 15 nucleotides, at least 15-30, advantageously about 30-45 nucleotides, and preferably about 45-75, at least 57, 87 or 150 consecutive or contiguous nucleotides of the sequence encoding the total protein or polyprotein. Epitope determination procedures, such as, generating overlapping peptide libraries (Hemmer et al., 1998), Pepscan (Geysen et al., 1984; Geysen et al., 1985; Van der Zee R. et al., 1989; Geysen, 1990; Multipin.RTM. Peptide Synthesis Kits de Chiron) and algorithms (De Groot et al., 1999), and in PCT Application Serial No. PCT/US2004/022605 all of which are incorporated herein by reference in their entireties, can be used in the practice of the invention, without undue experimentation. Other documents cited and incorporated herein may also be consulted for methods for determining epitopes of an immunogen or antigen and thus nucleic acid molecules that encode such epitopes.

The term "vaccine composition" or "vaccine" covers herein any composition able, once it has been injected to a subject, including canids, felids and humans, to protect the subject from cutaneous leishmaniasis and/or visceral leishmaniasis, including to prevent implantation of the parasite, and/or to prevent disease progression in infected subjects, and/or to limit the diffusion of runaway parasites to internal organs. This may be accomplished by the vaccine through the induction of humoral immune response against KMP11, notably the induction of anti-KMP11 IgG1, and/or through the induction of cell-mediated immune response against KMP11, including through the induction of a CD8 cell-mediated immune response against KMP11 and/or the induction of a CD4 cell-mediated immune response against KMP11. The induction of a humoral immune response is desirable in instances of cutaneous leishmaniasis, and the induction of cell-mediated immune is desirable in instances of response in case of visceral leishmaniasis. An advantage of the vaccine strategy and of the use of the vaccines of the present invention is to induce both humoral immune response and cell-mediated immune response, which permits protection of the subject from both cutaneous leishmaniasis and visceral leishmaniasis.

The pharmaceutically or veterinary acceptable excipient, diluent or vehicle may be water, saline or a buffer, or another substance known to those of skill in the art and recognized by those of skill in the art as an acceptable excipient.

In a further aspect, the present invention relates to an in vivo expression vector comprising a polynucleotide sequence, which contains and expresses the *Leishmania* antigen KMP11 or immunogen or epitopes thereof, as described herein.

The in vivo expression vector includes any transcription unit containing a polynucleotide or a gene of interest and those essential elements for its in vivo expression. These expression vectors can be plasmids or recombinant viral vectors.

As used herein, the term "polynucleotide" includes DNA and RNA, and derivatives thereof, such as those containing modified backbones. It should be appreciated that the invention provides polynucleotides comprising sequences complementary to those described herein.

Polynucleotides according to the invention can be prepared in different ways (e.g. by chemical synthesis, by gene cloning etc.) and can take various forms (e.g. single stranded, double stranded, primers, probes etc.) (see Maniatis et al., Molecular Cloning: a Laboratory Manuel, Cold Spring Harbor Laboratory, 1982).

The polynucleotide is generally an open reading frame (ORF), starting from a start codon (methionine codon) and ending with a termination signal (stop codon). The polynucleotide can also include regions that regulate its expression, such as transcription initiation, translation and transcription termination. Thus, also included are promoters and ribosome binding regions (in general these regulatory elements lie approximately between 60 and 250 nucleotides upstream of the start codon of the coding sequence or gene; Doree S M et al., J. Bacteriol. 2001, 183(6): 1983-9; Pandher K et al., Infect. Imm. 1998, 66(12): 5613-9; Chung J Y et al., FEMS Microbiol letters 1998, 166: 289-296), transcription terminators (in general the terminator is located within approximately 50 nucleotides downstream of the stop codon of the coding sequence or gene; Ward C K et al, Infect. Imm. 1998, 66(7): 3326-36). In the case of an operon, such regulatory regions may be located a greater distance upstream of the gene or coding sequence.

As used herein, the term "derivative" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide is immunoreactive with the wild-type polypeptide.

The term "conservative variation" denotes the replacement of an amino acid residue by another biologically similar residue, or the replacement of a nucleotide in a nucleic acid sequence such that the encoded amino acid residue does not change or is another biologically similar residue. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

More generally, the present invention encompasses polynucleotide derivative. As used herein, the term "derivative" refers to a polypeptide, or a nucleic acid encoding a polypeptide, that has at least about 50% identity, at least about 60% identity, at least about 70% identity, at elast about 75% identity, at least about 80% identity, at least about 85% identity, 90% identity, at least about 95% identity, and at least about 96%, 97%, 98%, or 99% or more identity to the amino acid sequence SEQ ID No2. Sequences having such homology or identity can encompass genetic code degeneration. The percentage of identity between two amino acid sequences can be established by the NCBI (National Center for Biotechnology Information) pairwise blast and the blosum62 matrix, using the standard parameters (see, e.g., the BLAST or BLASTX algorithm available on the "National Center for Biotechnology Information" (NCBI, Bethesda, Md., USA) server, as well as in Altschul et al. J. Mol. Biol. 1990. 215. 403-410; and thus, this document speaks of using the algorithm or the BLAST or BLASTX and BLOSUM62 matrix by the term "blasts").

"Code" as used herein does not mean that the polynucleotide is limited to an actual coding sequence but also encompasses the whole gene including its regulatory sequences which are non-coding sequences.

Sequence homology or identity such as nucleotide sequence homology also can be determined using the "Align" program of Myers and Miller, ("Optimal Alignments in Linear Space", CABIOS 4, 11-17, 1988, incorporated herein by reference) and available at NCBI, as well as the same or other programs available via the Internet at sites thereon such as the NCBI site.

Alternatively or additionally, the term "homology" or "identity", for instance, with respect to a nucleotide or amino acid sequence, can indicate a quantitative measure of homology between two sequences. The percent sequence homology can be calculated as: $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{ref}=8$; $N_{dif}=2$).

Alternatively or additionally, "homology" or "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman, 1983 PNAS USA 80:726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

Advantageously, sequence identity or homology such as amino acid sequence identity or homology can be determined using the BlastP program (Altschul et al., Nucl. Acids Res. 25, 3389-3402, incorporated herein by reference) and available at NCBI, as well as the same or other programs available via the Internet at sites thereon such as the NCBI site.

The following documents (each incorporated herein by reference) provide algorithms for comparing the relative identity or homology of sequences such as amino acid residues of two proteins, and additionally or alternatively with respect to the foregoing, the teachings in these references can be used for determining percent homology or identity: Needleman S B and Wunsch C D, "A general method applicable to the search for similarities in the amino acid sequences of two proteins," J. Mol. Biol. 48:444-453 (1970); Smith T F and Waterman M S, "Comparison of Bio-sequences," Advances in Applied Mathematics 2:482-489 (1981); Smith T F, Waterman M S and Sadler J R, "Statistical characterization of nucleic acid sequence functional domains," Nucleic Acids Res., 11:2205-2220 (1983); Feng D F and Dolittle R F, "Progressive sequence alignment as a prerequisite to correct phylogenetic trees," J. of Molec. Evol., 25:351-360 (1987); Higgins D G and Sharp P M, "Fast and sensitive multiple sequence alignment on a microcomputer," CABIOS, 5: 151-153 (1989); Thompson J D, Higgins D G and Gibson T J, "ClusterW: improving the sensitivity of progressive multiple sequence alignment through sequence weighing, positions-specific gap penalties and weight matrix choice," Nucleic Acid Res., 22:4673-480 (1994); and, Devereux J, Haeberlie P and Smithies O, "A comprehensive set of sequence analysis program for the VAX," Nucl. Acids Res., 12: 387-395 (1984). And, without undue experimentation, the skilled artisan can consult with many other programs or references for determining percent homology.

The vaccines according to the instant invention include vectors encoding at least the KMP11 polynucleotide or gene from *L. infantum* and/or the KMP11 polynucleotide or gene from *L. chagasi*, and/or the KMP11 polynucleotide or gene from *L. donovani*. Advantageously, for Southern Europe, Africa and Asia, vaccines include vectors encoding the KMP11 polynucleotide or gene from at least *L. infantum* . Advantageously, for Southern and Central Americas, vaccines include vectors encoding the KMP11 polynucleotide or gene from at least *L. chagasi*.

Codon preference among different species can be dramatically different. To enhance the expression level of a foreign protein, it is important to match the codon frequency of the foreign protein to that of the host expression system (Kim et al., Gene, 1997, 199(1-2): 293-301). For codon optimization, other factors than codon frequency can be taken into consideration, e.g. DNA motifs and repeats, secondary structure, GC content, repetitive codons, restriction endonuclease sites, functional motifs like splice site or terminator structure. Algorithms have been created to facilitate the design of the optimal nucleotide sequence. Geneart GmbH (Regensburg, Germany) has developed the proprietary GENEOPTIMIZER™ software (WO-A-04/059556 and WO-A-06/013103) that implements multi-parameter optimization in one single operation. Taking into account the most important parameters in parallel, the software generates a total of up to 500,000 optimized variants of the target sequence in an evolutionary approach and selects the one that is best suited. It has been reported that such optimized genes have up to a 100-fold increase in expression yields compared to the original gene sequence (Bradel-Tretheway et al., J. Virol. Methods, 2003, 111(2): 145-56; Disbrow et al., Virology, 2003, 311(1): 105-14).

The published nucleic acid sequences for KMP11 protein of *L. infantum* (NCBI GenBank database accession number CAA64883) were optimized by the GENEOPTIMIZER™ software.

The codon-optimized synthetic nucleic acid sequence for KMP11 protein of *L. infantum* is designated as SEQ ID No3. The codon-optimized nucleic acid sequences encode a polypeptide having the same amino acid sequence as those disclosed in GenBank CAA64883, also designated SEQ ID No4. The codon-optimization changes only the nucleic acid sequence and not the encoded amino acid sequence.

A further object of the present invention relates to a codon-optimized polynucleotide sequence encoding a *Leishmania* KMP11 antigen. One embodiment of this invention is the codon-optimized polynucleotide sequence SEQ ID No3, encoding a *L. infantum* KMP11 antigen SEQ ID No4.

Another object relates to an in vivo expression vector comprising a codon-optimized polynucleotide sequence encoding a *Leishmania* KMP11 antigen. An embodiment of this object is an in vivo expression vector comprising the codon-optimized polynucleotide sequence SEQ ID No3, encoding a *L. infantum* KMP11 antigen SEQ ID No4.

More generally, the present invention encompasses in vivo expression vectors including any plasmid (EP-A2-1001025; Chaudhuri P Res. Vet. Sci. 2001, 70(3), 255-6) containing the polynucleotide or gene of *Leishmania* KMP11 and elements necessary for its in vivo expression.

As used herein, the term "plasmid" includes any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

In a specific, non-limiting example, the pVR1020 or pVR1012 plasmid (VICAL Inc.; Luke C. et al., Journal of Infectious Diseases, 1997, 175, 91-97; Hartikka J. et al., Human Gene Therapy, 1996, 7, 1205-1217) or pAB110 (U.S. Pat. No. 6,852,705) can be utilized as a vector for the insertion of a polynucleotide sequence. The pVR1020 plasmid is derived from pVR1012 and contains the human tPA signal sequence. Each plasmid comprises or contains or consists essentially of, the polynucleotide according to the present invention, operably linked to a promoter or under the control of a promoter or dependent upon a promoter, wherein the promoter is advantageously adjacent thereto the polynucleotide of the present invention. In general, it is advantageous to employ a strong promoter that is functional in eukaryotic cells. One example of a useful promoter is the immediate early cytomegalovirus promoter (CMV-IE) of human or murine origin, or optionally having another origin such as the rat or guinea pig. The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT Application No WO-A-87/03905. The CMV-IE promoter is advantageously a human CMV-IE (Boshart M. et al., Cell, 1985, 41, 521-530) or murine CMV-IE. In more general terms, the promoter has either a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa M. et al., Vaccine, 2000, 18, 2337-2344), or the actin promoter (Miyazaki J. et al., Gene, 1989, 79, 269-277). Functional sub fragments of these promoters, i.e., portions of these promoters that maintain adequate promoter activity, are included within the present invention, e.g. truncated CMV-IE promoters according to PCT Application No. WO-A-98/00166 or U.S. Pat. No. 6,156,567 can be used in the practice of the invention. A promoter useful in the practice of the invention consequently includes derivatives and sub fragments of a full-length promoter that maintain an adequate promoter activity and hence function as a promoter, advantageously having promoter activity substantially similar to that of the actual or full-length promoter from which the derivative or sub fragment is derived, e.g., akin to the activity of the truncated CMV-IE promoters of U.S. Pat. No. 6,156,567 in comparison to the activity of full-length CMV-IE promoters. Thus, a CMV-IE promoter in the practice of the invention can comprise or consist essentially of or consist of the promoter portion of the full-length promoter and/or the enhancer portion of the full-length promoter, as well as derivatives and sub fragments.

Advantageously, the plasmids comprise or consist essentially of other expression control elements. It is especially advantageous to incorporate stabilizing sequence(s), e.g., intron sequence(s), for example, the first intron of the hCMV-IE (PCT Application No. WO-A-89/01036), the intron II of the rabbit β-globin gene (van Ooyen et al., Science, 1979, 206, 337-344). As to the polyadenylation signal (polyA) for the plasmids and viral vectors other than poxviruses, use can more be made of the poly(A) signal of the bovine growth hormone (bGH) gene (see U.S. Pat. No. 5,122,458), or the poly(A) signal of the rabbit β-globin gene or the poly(A) signal of the SV40 virus.

In one embodiment of the present invention, the plasmid vector is pVR1020 KMP11, as described in example 1 herein.

More generally, the present invention encompasses in vivo expression vectors including any recombinant viral vector containing the polynucleotide or gene of *Leishmania* KMP11 and all those elements necessary for its in vivo expression.

Said recombinant viral vectors could be selected from, for example, the poxviruses, especially avipox viruses, such as fowlpox viruses or canarypox viruses. In one embodiment, the fowlpox virus is a TROVAC (see WO-A-96/40241). In another embodiment, the canarypox vector is an ALVAC. The use of these recombinant viral vectors and the insertion of polynucleotides or genes of interest is fully described in U.S. Pat. No. 5,174,993; U.S. Pat No. 5,505,941 and U.S. Pat. No. 5,766,599 for fowlpox, and in U.S. Pat. No. 5,756,103 for canarypox. More than one insertion site inside the viral genome could be used for the insertion of multiple genes of interest.

In one embodiment the viral vector is an adenovirus, such as a human adenovirus (HAV) or a canine adenovirus (CAV).

In another embodiment the viral vector is a human adenovirus, specifically a serotype 5 adenovirus, rendered incompetent for replication by a deletion in the E1 region of the viral genome, especially from about nucleotide 459 to about nucleotide 3510 by reference to the sequence of the hAd5 disclosed in Genbank under the accession number M73260 and in the referenced publication Chroboczek et al, 1992. The deleted adenovirus is propagated in E1-expressing 293 (Graham et al., 1977) or PER cells, especially PER.C6 (Falloux et al., 1998). The human adenovirus can additionally or alternatively be deleted in the E3 region, especially from about nucleotide 28592 to about nucleotide 30470. The deletion in the E1 region can be done in combination with a deletion in the E3 region (see, e.g. Shriver et al., 2002; Graham et al., 1991; Ilan et al., 1997; U.S. Pat. Nos. 6,133,028 and 6,692,956; Tripathy et al., 1994; Tapnell, 1993; Danthinne et al., 2000; Berkner, 1988; Berkner et al., 1983; Chavier et al., 1996). The insertion sites can be the E1 and/or E3 loci (region) eventually after a partial or complete deletion of the E1 and/or E3 regions. Advantageously, when the expression vector is an adenovirus, the polynucleotide to be expressed is inserted under the control of a promoter functional in eukaryotic cells, such as a strong promoter, adventageously a cytomegalovirus immediate-early gene promoter (CMV-IE promoter), especially the enhancer/promoter region from about nucleotide −734 to about nucleotide +7 in Boshart et al., 1985 or the enhancer/promoter region from the pCI vector from Promega Corp. The CMV-IE promoter is advantageously of murine or human origin. The promoter of the elongation factor 1α can also be used. A muscle specific promoter can also be used (Li et al., 1999). Strong promoters are also discussed herein in relation to plasmid vectors. In one embodiment, a splicing sequence can be located downstream of the enhancer/promoter region. For example, the intron 1 isolated from the CMV-IE gene (Stenberg et al., 1984), the intron isolated from the rabbit or human β-globin gene, especially the intron 2 from the b-globin gene, the intron isolated from the immunoglobulin gene, a splicing sequence from the SV40 early gene or the chimeric intron sequence isolated from the pCI vector from Promege Corp. comprising the human β-globin gene donor sequence can be fused to the mouse immunoglobulin acceptor sequence (from about nucleotide 890 to about nucleotide 1022 in Genbank under the accession number CVU47120). A poly(A) sequence and terminator sequence can be inserted downstream the polynucleotide to be expressed, e.g. a bovine growth hormone gene, especially from about nucleotide 2339 to about nucleotide 2550 in Genbank under the accession number BOVGHRH, a rabbit β-globin gene or a SV40 late gene polyadenylation signal.

In another embodiment the viral vector is a canine adenovirus, especially a CAV-2 (see, e.g. Fischer et al., 2002; U.S. Pat. Nos. 5,529,780 and 5,688,920; PCT Application No. WO95/14102). For CAV, the insertion sites can be in the E3 region and/or in the region located between the E4 region and the right ITR region (see U.S. Pat. Nos. 6,090,393 and 6,156, 567). In one embodiment the insert is under the control of a promoter, such as a cytomegalovirus immediate-early gene promoter (CMV-IE promoter) or a promoter already described for a human adenovirus vector. A poly(A) sequence and terminator sequence can be inserted downstream the polynucleotide to be expressed, e.g. a bovine growth hormone gene or a rabbit β-globin gene polyadenylation signal.

In another embodiment, the viral vector is a herpesvirus such as a canine herpesvirus (CHV) or a feline herpesvirus (FHV). For CHV, the insertion sites may be in the thymidine kinase gene, in the ORF3, or in the UL43 ORF (see U.S. Pat. No. 6,159,477). In one embodiment the polynucleotide to be expressed is inserted under the control of a promoter functional in eukaryotic cells, advantageously a CMV-IE promoter (murine or human). A poly(A) sequence and terminator sequence can be inserted downstream the polynucleotide to be expressed, e.g. bovine growth hormone or a rabbit β-globin gene polyadenylation signal.

For recombinant vectors based on a poxvirus vector, a vaccinia virus or an attenuated vaccinia virus, (for instance, MVA, a modified Ankara strain obtained after more than 570 passages of the Ankara vaccine strain on chicken embryo fibroblasts; see Stickl & Hochstein-Mintzel, Munch. Med. Wschr., 1971, 113, 1149-1153; Sutter et al., Proc. Natl. Acad. Sci. U.S.A., 1992, 89, 10847-10851; available as ATCC VR-1508; or NYVAC, see U.S. Pat. No. 5,494,807, for instance, Examples 1 to 6 and et seq of U.S. Pat. No. 5,494,807 which discuss the construction of NYVAC, as well as variations of NYVAC with additional ORFs deleted from the Copenhagen strain vaccinia virus genome, as well as the insertion of heterologous coding nucleic acid molecules into sites of this recombinant, and also, the use of matched promoters; see also WO-A-96/40241), an avipox virus or an attenuated avipox virus (e.g., canarypox, fowlpox, dovepox, pigeonpox, quailpox, ALVAC or TROVAC; see, e.g., U.S. Pat. Nos. 5,505,941, 5,494,807) can be used. Attenuated canarypox viruses are described in U.S. Pat. No. 5,756,103 (ALVAC) and WO-A-01/05934. Reference is also made to U.S. Pat. No. 5,766,599 which pertains to the attenuated fowlpox strain TROVAC. Reference is made to the canarypox available from the ATCC under access number VR-111. Numerous fowlpox virus vaccination strains are also available, e.g. the DIFTOSEC CT strain marketed by MERIAL and the NOBILIS VARIOLE vaccine marketed by INTERVET. For information on the method used to generate recombinants thereof and how to administer recombinants thereof, the skilled artisan can refer documents cited herein and to WO-A-90/12882, e.g., as to vaccinia virus mention is made of U.S. Pat. Nos. 4,769,330, 4,722,848, 4,603,112, 5,110,587, 5,494, 807, and 5,762,938 inter alia; as to fowlpox, mention is made of U.S. Pat. Nos. 5,174,993, 5,505,941 and 5,766,599 inter alia; as to canarypox mention is made of U.S. Pat. No. 5,756, 103 inter alia. When the expression vector is a vaccinia virus, insertion site or sites for the polynucleotide or polynucleotides to be expressed are advantageously at the thymidine kinase (TK) gene or insertion site, the hemagglutinin (HA) gene or insertion site, the region encoding the inclusion body of the A type (ATI); see also documents cited herein, especially those pertaining to vaccinia virus. In the case of canarypox, advantageously the insertion site or sites are ORF(s) C3, C5 and/or C6; see also documents cited herein, especially those pertaining to canarypox virus. In the case of fowlpox, advantageously the insertion site or sites are ORFs F7 and/or F8; see also documents cited herein, especially those pertaining to fowlpox virus. The insertion site or sites for MVA virus area advantageously as in various publications, including Carroll M. W. et al., Vaccine, 1997, 15 (4), 387-394; Stittelaar K. J. et al., J. Virol., 2000, 74 (9), 4236-4243; Sutter G. et al., 1994, Vaccine, 12 (11), 1032-1040; and, in this regard it is also noted that the complete MVA genome is described in Antoine G., Virology, 1998, 244, 365-396, which enables the skilled artisan to use other insertion sites or other promoters. Advantageously, the polynucleotide to be expressed is inserted under the control of a specific poxvirus promoter, e.g., the vaccinia promoter 7.5 kDa (Cochran et al., J. Virology, 1985, 54, 30-35), the vaccinia promoter I3L (Riviere et al., J. Virology, 1992, 66, 3424-3434), the vaccinia promoter HA (Shida, Virology, 1986, 150, 451-457), the cowpox promoter ATI (Funahashi et al., J. Gen. Virol., 1988, 69, 35-47), the vaccinia promoter H6 (Taylor J. et al., Vaccine, 1988, 6, 504-508; Guo P. et al. J. Virol., 1989, 63, 4189-4198; Perkus M. et al., J. Virol., 1989, 63, 3829-3836), inter alia.

In a further embodiment, the recombinant viral vector is the recombinant ALVAC canarypox virus vCP2350, as described in the example 3.

The vaccines containing recombinant viral vectors according to the invention may be freeze-dried, advantageously with a stabiliser. Freeze-drying can be done according to well-known standard freeze-drying procedures. The pharmaceutically or veterinary acceptable stabilisers may be carbohydrates (e.g. sorbitol, mannitol, lactose, sucrose, glucose, dextran, trehalose), sodium glutamate (Tsvetkov T et al., Cryobiology 1983, 20(3): 318-23; Israeli E et al., Cryobiology 1993, 30(5): 519-23), proteins such as peptone, albumin, lactalbumin or casein, protein containing agents such as skimmed milk (Mills C K et al., Cryobiology 1988, 25(2): 148-52; Wolff E et al., Cryobiology 1990, 27(5): 569-75), and buffers (e.g. phosphate buffer, alkaline metal phosphate buffer). An adjuvant may be used to make soluble the freeze-dried preparations.

Any vaccine composition according to the invention can also advantageously contain one or more adjuvanta.

For the Plasmids:

The plasmid-based vaccines can be formulated with cationic lipids, advantageously with DMRIE (N-(2-hydroxyethyl)-N,N-dimethyl-2,3-bis(tetradecyloxy)-1-propanammonium; WO-A-96/34109), and advantageously in association with a neutral lipid, for example DOPE (dioleoyl-phosphatidyl-ethanolamine; Behr J. P., Bioconjugate Chemistry, 1994: 5: 382-389), in order to form DMRIE-DOPE. In one embodiment, the mixture is made extemporaneously, and before its administration it is advantageous to wait about 10 min to about 60 min, for example, about 30 min, for the appropriate complexation of the mixture. When DOPE is used, the molar ratio of DMRIE/DOPE can be from 95/5 to 5/95 and is advantageously 1/1. The weight ratio plasmid/ DMRIE or DMRIE-DOPE adjuvant is, for example, from 50/1 to 1/10, from 10/1 to 1/5 or from 1/1 to 1/2.

Optionally a cytokine can be added to the composition, especially GM-CSF or cytokines inducing Th1 (e.g. IL12). These cytokines can be added to the composition as a plasmid encoding the cytokine protein. In one embodiment, the cytokines are from canine origin, e.g. canine GM-CSF which gene sequence has been deposited at the GenBank database (accession number S49738). This sequence can be used to create said plasmid in a manner similar to what was made in WO-A-00/77210 (incorporated herein by reference).

For the Recombinant Viral Vectors:

The recombinant viral vector-based vaccine can be combined with fMLP (N-formyl-methionyl-leucyl-phenylalanine; U.S. Pat. No. 6,017,537 incorporated herein by reference) and/or Carbomer adjuvant (Phameuropa Vol. 8, No. 2, June 1996). Persons skilled in the art can also refer to U.S. Pat. No. 2,909,462 (incorporated herein by reference) which describes such acrylic polymers cross-linked with a polyhydroxylated compound having at least 3 hydroxyl groups, advantageously not more than 8, the hydrogen atoms of at least three hydroxyls being replaced by unsaturated aliphatic radicals having at least 2 carbon atoms. For example, the radicals are those containing from 2 to 4 carbon atoms, e.g. vinyls, allyls and other ethylenically unsaturated groups. The unsaturated radicals may themselves contain other substituents, such as methyl. The products sold under the name Carbopol® (BF Goodrich, Ohio, USA) are appropriate. The products are cross-linked with an allyl sucrose or with allyl pentaerythritol. Among them, there may be advantageously mentioned Carbopol® 974P, 934P and 971P.

Among the copolymers of maleic anhydride and alkenyl derivative, the copolymers EMA® (Monsanto) which are copolymers of maleic anhydride and ethylene, linear or cross-linked, for example cross-linked with divinyl ether, are advantageous. Reference may be made to J. Fields et al., Nature, 186: 778-780, 4 Jun. 1960, incorporated herein by reference.

The polymers of acrylic or methacrylic acid and the copolymers EMA® are formed, for example, of basic units of the following formula:

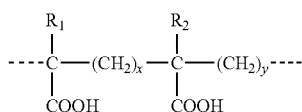

in which:
$R_1$ and $R_2$, which are identical or different, represent H or $CH_3$
x=0 or 1, preferably x=1
y=1 or 2, with x+y=2

For the copolymers EMA®, x=0 and y=2. For the carbomers, x=y=1.

The dissolution of these polymers in water leads to an acid solution, which is neutralized, advantageously to physiological pH, in order to provide the adjuvant solution into which the vaccine itself is incorporated. The carboxyl groups of the polymer are then partly in $COO^-$ form.

In one embodiment, a solution of adjuvant, especially of carbomer, is prepared in distilled water, advantageously in the presence of sodium chloride, the solution obtained being at an acidic pH. This stock solution is diluted by adding it to the desired quantity (for obtaining the desired final concentration), or a substantial part thereof, of water charged with NaCl, advantageously physiological saline (NaCl 9 g/l) all at once in several portions with concomitant or subsequent neutralization (pH 7.3 to 7.4), advantageously with NaOH. This solution at physiological pH is used for mixing with the vaccine, which may be especially stored in freeze-dried, liquid or frozen form.

The polymer concentration in the final vaccine composition can be from 0.01% to 2% w/v, from 0.06 to 1% w/v, or from 0.1 to 0.6% w/v.

Another aspect of the present invention is methods of prime-boost vaccination of Leishmania-susceptible subjects using the vaccine compositions according to the invention.

By definition, Leishmania-susceptible subjects encompass humans, felids (i.e. domesticated cats, kittens, big cats and wild cats, for example) and canids (i.e. dogs, bitchs, puppies, foxes, jackals, and wolves, for example). In one embodiment, canines are a suitable subject for administration of the vaccine according to the present invention.

These prime-boost administration methods include at least two different administrations, which consist of at least one primo-administration of an effective amount of a vaccine composition according to the invention and after a certain period of time at least one boost administration of an effective amount of a vaccine composition according to the invention, wherein 1) the vaccine compositions for the primo-administration are plasmid-based vaccines and the vaccine compositions for the boost administration are recombinant viral vector-based vaccines; and/or 2) the vaccine compositions for the primo-administration are plasmid-based vaccines coupled to electrotranfer treatment and the vaccine compositions for the boost administration are recombinant viral vector-based vaccines; and/or 3) the vaccine compositions are the same for the primo-administration and for the boost administration and the route of administration and/or the means of administration are not the same for the primo-administration and for the boost administration. The routes of administration can be, for example, intramuscular (IM) or intradermal (ID) or subcutaneous. The means of administration can be, for example, a syringe with a needle, or needle free apparatus, or a syringe with a needle coupled to electrotransfer (ET) treatment, or needle free apparatus coupled to ET treatment.

The prime-boost administrations are advantageously carried out 2 to 6 weeks apart, for example, about 3 weeks apart. According to one embodiment, a semi-annual booster or an annual booster, advantageously using the viral vector-based vaccine, is also envisaged. The animals are advantageously at least 6 to 8 weeks old at the time of the first administration.

Another embodiment of the prime-boost administration regimen consists of primo-administration of a plasmid-based vaccine and a boost administration of a recombinant poxvirus vector-based vaccine, for example, with a canarypox virus vector. Both priming and boosting administrations are advantageously done via intradermal (ID) route using a needle free apparatus. In one embodiment, this plasmid-based vaccine is a vaccine comprising pVR1020 KMP11 as described in example 1, and this canarypox virus vector is vCP2350 as described in example 3.

In yet another embodiment of the present invention, the primo-administration is made with a plasmid-based vaccine via the ID route using a needle free apparatus and the boost administration is made with a plasmid-based vaccine via the intramuscular (IM) route using a syringe and a needle coupled to ET treatment. In a further embodiment, this plasmid-based vaccine is a vaccine comprising pVR1020 KMP11 as described in example 1.

A further embodiment of the prime-boost administration regimen consists of primo-administration of a plasmid-based vaccine coupled to ET treatment and boost administration of a recombinant poxvirus vector-based vaccine, advantageously with a canarypox virus vector. The primo-administration is advantageously done intramuscularly and the boost administration is advantageously done via intradermal (ID) route using a needle free apparatus. In another embodiment, this plasmid-based vaccine is a vaccine comprising pVR1020 KMP11 as described in example 1, and this canarypox virus vector is vCP2350 as described in example 3.

In another embodiment, the primo-administration comprises a plasmid-based vaccine via intramuscular (IM) route using a syringe and a needle coupled to ET treatment and the boost administration comprises a plasmid-based vaccine via ID route using a needle free apparatus. In one embodiment, this plasmid-based vaccine is a vaccine comprising pVR1020 KMP11 as described in example 1.

In one embodiment of the prime-boost regimen, the primo-administration utilizes a needle free apparatus via the ID route with a plasmid-based vaccine, a first boost administration comprises a plasmid-based vaccine via IM route using a syringe and a needle coupled to ET treatment, and a second boost administration utilizes a needle free apparatus via ID route with a recombinant viral vector-based vaccine, advantageously with a canarypox vector. In a further embodiment, this plasmid-based vaccine is a vaccine comprising pVR1020 KMP11 as described in example 1, and this canarypox virus vector is vCP2350 as described in example 3.

Another aspect of the invention is the use of a plasmid-based vaccine according to the present invention for administration to *Leishmania*-susceptible animals, wherein this administration is coupled to ET treatment. The administration of a plasmid-based vaccine is advantageously intramuscular. The means of administration is, for example, a syringe and a needle. One or several injections can be administered successively. In the case of several injections, they can be carried out 2 to 6 weeks apart, for example, about 3 weeks apart. According to one embodiment, a semi-annual booster or an annual booster is also envisaged.

For plasmid-based vaccines, an advantageous route of administration is ID. This administration can be made by a syringe with a needle or with a needle free apparatus like DERMOJET™ or BIOJECTOR™ (Bioject, Oregon, USA) or VETJET™ (Merial) or VITAJET™ (Bioject Inc.), see US-A-2006/0034867. The dosage can be from 50 µg to 500 µg per plasmid. When DMRIE-DOPE is added, 100 µg per plasmid can be utilized. When canine GM-CSF or other cytokines are used, the plasmid encoding this protein is present at a dosage of from about 200 µg to about 500 µg and can advantageously be 200 µg. The volume of doses can be between 0.01 ml and 0.5 ml, for example, 0.25 ml. Administration can be provided with multiple points of injection.

Another envisioned route of administration for plasmid-based vaccines is the IM route coupled to electrotransfer (ET) treatment. The ET treatment can be performed using an apparatus for electrotransfer and the specifications of the manufacturer (i.e. Sphergen G250 generator (Sphergen SARL, Evry Genopole, France); MedPulser® DNA electroporation system (Innovio Biomedical Corporation, San Diego, Calif., USA)). In one embodiment, the apparatus for electrotransfer has a unipolar field. The field intensity can be from about 50 to about 250 V/cm, from about 50 to about 200 V/cm, or from about 50 to about 175 V/cm. The pulse duration is from about 1 to about 50 msec, or from about 15 to about 25 msec. The frequency is from about 1 to about 50 Hz, or from about 5 to about 15 Hz. The interpulse interval is from about 1 to 1000 msec, or from about 1 to about 200 msec. The number of pulses is from 1 to 20, or from 5 to 10. The intra tissular intensity is advantageously up to about 2 A. The distance between electrodes is from about 0.2 to about 1 cm, or from about 0.2 to about 0.5 cm.

For recombinant viral vector-based vaccines, the route of administration is advantageously ID. This administration can be made by a syringe with a needle or with a needle free apparatus like DERMOJET™ or BIOJECTOR™ (Bioject, Oregon, USA) or VETJET™ (Merial) or VITAJET™ needle free Injectors (Bioject Inc.). The dosage is from about $10^3$ pfu to about $10^9$ pfu per recombinant poxvirus vector. When the vector is a canarypox virus, the dosage is, for example, from about $10^5$ pfu to about $10^9$ pfu, or from about $10^6$ pfu to about $10^8$ pfu. The volume of doses is from about 0.01 ml to 0.2 ml, and is advantageously 0.1 ml. Administration can comprise multiple points of injection.

For the IM route the volume of the vaccine provided is from 0.2 to 2 ml, or from about 0.5 to 1 ml. The same dosages are utilized for any of the vectors of the present invention.

Another aspect of the present invention is a kit for prime-boost vaccination according to the present invention. The kit comprises at least two vials: a first vial containing a vaccine for the primo-vaccination according to the present invention, and a second vial containing a vaccine for the boost-vaccination according to the present invention. The kit can advantageously contain additional first or second vials for additional primo-vaccinations or additional boost-vaccinations.

In one embodiment, the kit comprises two vials, one containing a plasmid-based vaccine for the primo-vaccination according to the present invention, the other vial containing a recombinant viral vector-based vaccine for the boost-vaccination according to the present invention.

In another embodiment, the kit comprises two vials, one containing a pVR1020 KMP11 plasmid-based vaccine for the primo-vaccination according to the present invention, the other vial containing a vCP2350 vector-based vaccine for the boost-vaccination according to the present invention.

The invention will now be further described by way of the following non-limiting examples.

EXAMPLES

Without further elaboration, it is believed that one skilled in the art can, using the preceding descriptions, practice the present invention to its fullest extent. The following detailed examples are to be construed as merely illustrative, and not limitations of the preceding disclosure in any way whatsoever. Those skilled in the art will promptly recognize appropriate variations from the procedures both as to reactants and as to reaction conditions and techniques.

Construction of DNA inserts, plasmids, recombinant viral vectors was carried out using the standard molecular biology techniques described by J. Sambrook et al. (Molecular Cloning: A Laboratory Manual, 2nd Edition, Cold Spring Harbor Laboratory, Cold Spring Harbor, N.Y., 1989). All the restriction fragments used for the present invention were isolated using the "GENECLEAN®" DNA purifying kit (BIO 101 Inc., La Jolla, Calif.).

Example 1

Construction of a Plasmid Expressing the *L. infantum* KMP11 Antigen

The nucleic acid sequence encoding the *L. infantum* KMP11 was synthesized chemically, having the sequence described in SEQ ID NO: 1 and having polyadenine tails. The KMP11 fragment was amplified by PCR and cloned into the TOPO cloning site of the pVR2001-TOPA (or pVR2001-TOPO) (Oliveira F. et al. Vaccine (2006) 24: 374-90), having the tissue plasminogen activator signal peptide (TPA), to obtain the plasmid pVR1020 KMP11. VR2001-TOPO is derived from the plasmid VR1020. VR1020 is a plasmid backbone available from Vical, Inc., (Sandiego, Calif.) which has been previously used, see, e.g., U.S. Pat. Nos. 6,451,769 and 7,078,507; as described in Oliveira et al., plasmid VR2001-TOPO (or pVR2001-TOPA) is VR1020 modified by the addition of topoisomerases flanking the cloning site and containing coding for and expressing a signal secretory peptide that increases the likelihood of producing a secreted protein (see FIG. 1 in Oliveira F. et al. Vaccine (2006) 24: 374-90).

Figure 10:
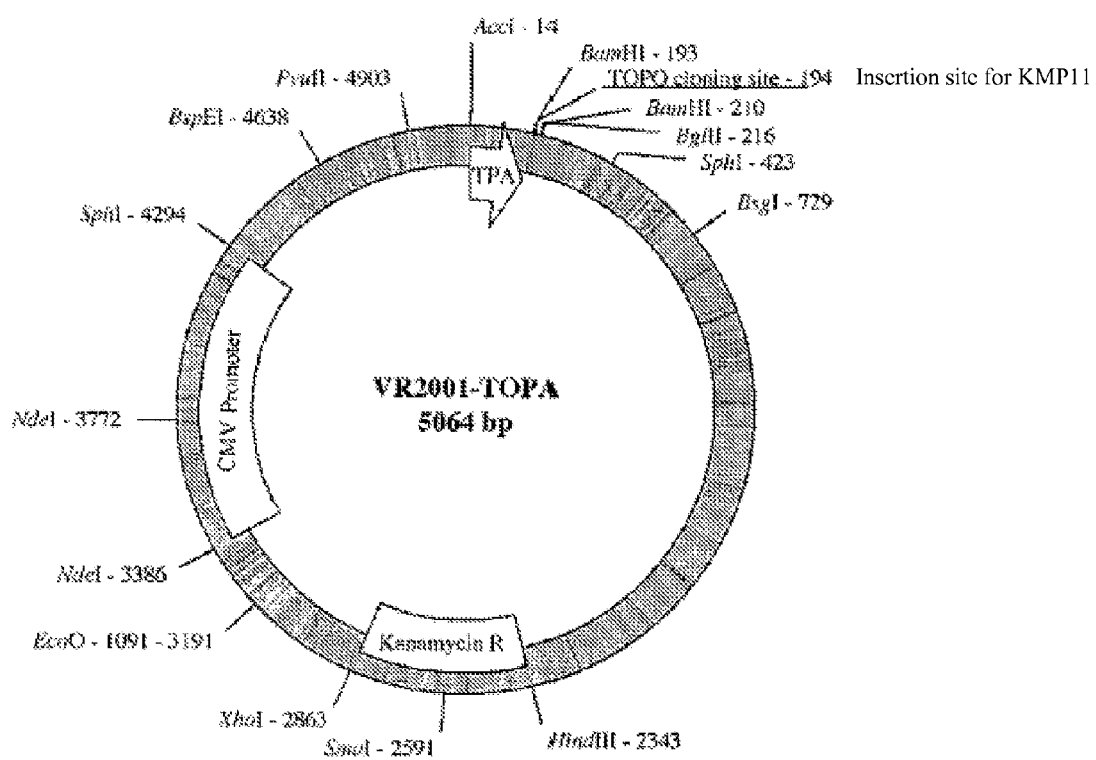
FIG. 10 is the plasmid diagram of the donor plasmid VR2001-TOPA or VR2001-TOPO.

The nucleic acid sequence of one strand of the plasmid pVR1020 KMP11 is described in SEQ ID NO: 5, and the plasmid map is provided in FIG. 10. In accordance with the present invention, VR1020 KMP11 therefore contains and expresses a DNA encoding a promoter for driving expression in a mammalian cell, a DNA encoding a leader peptide for facilitating secretion/release of a prokaryotic protein sequence from a mammalian cell, for example a CMV promoter, a DNA encoding KMP11, and a DNA encoding a terminator. VR1020 KMP11 additionally contains topoisomerases flanking the DNA encoding KMP11 and containing coding for a signal secretory peptide that increases the likelihood of producing a secreted protein.

Example 2

Prime-boost Vaccination of Dogs Against Leishmaniasis with Plasmid-based Vaccines Two groups of 5 conventional dogs were vaccinated either with a plasmid expressing the *L. infantum* KMP11 antigen or with the control plasmid having no insert. Priming administration was performed intradermally at D0 using the MERIAL VETJET™ needle free injector.

The MERIAL VETJET™ needle free injector uses compressed air as a power source. The needle-free injection leads to reduced lesions and trauma at the injection site when compared to current needle usage. The device is activated by placing the nozzle against the subject and will not fire until the mechanism travels approximately 0.30" against a spring load.

The MERIAL VETJET™ needle free injector has three basic steps in the operation cycle: (1) pull the trigger, (2) push the device against the target injection site and (3) pull the device away from the injection site and release the trigger. When the trigger is pulled, the trigger activates the initiator valve. The trigger sets the firing mechanism into the priming position. When the device is pushed against the target injection site, the firing mechanism slides back and releases the poppet valve and the drug is expelled through the nozzle. When the device is pulled away from the injection site and the trigger is released, the firing mechanism retracts. Exhaust air is expelled, activating the dye system (if desired). The drug fill system loads a fresh dose.

The inner thigh area of the two groups of 5 conventional dogs was clipped free of fur and disinfected with povidone iodine (VETEDINE®, Vetoquinol, Lure, France) before administration. Vaccinated dogs (n=5) received in the right medial thigh a dose of 400 µg of purified pVR1020 KMP11 plasmid (see Example 1) in a volume of 0.2 ml of TE pH 8 buffer (i.e., 2 mg/ml). Control dogs (n=5) received in a similar manner the empty expression plasmid pVR1020. Dogs were not anesthetized for this administration.

A booster administration was performed at D21 using the same plasmids as for the priming (i.e., pVR1020 KMP11 in vaccinated dogs and pVR1020 in control dogs) and the same dose (400 µg at 2 mg/ml), but using an intramuscular delivery coupled to electrotransfer (ET) treatment. Dogs were anesthetized by the intramuscular route using 5 mg/kg ketamine and 10 mg/kg medetomidine.

The IM administration and ET treatment was applied to the left inner thigh area (i.e., left semi-membranous muscle). The area was clipped free of fur and disinfected with povidone iodine (VETEDINE®) before treatment. The injection was performed using the SPHERGEN 3® needle device INJ-1 (Sphergen SARL, Evry Genopole, France) with needles separated by 0.5 cm each. The ET treatment will take place immediately following the injection, using a SPHERGEN G250 generator (Sphergen SARL, Evry Genopole, France). The following ET specifications were used: T1: 20 msec, T2: 80 msec, frequency: 10 Hz, 10 pulses. Applied voltage was 87.5 V, creating an electric field of 175 V/cm within the muscle.

Figure 3:
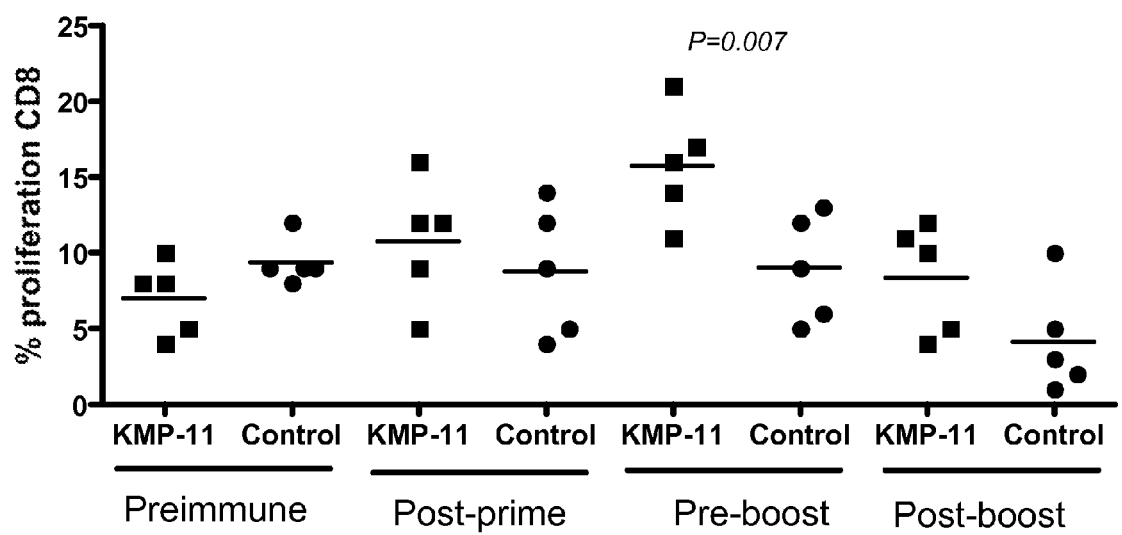
FIG. 3 shows the specific CD8 T cells proliferation before vaccination, between an initial vaccination and a subsequent boost vaccination, and after boost-vaccination; expressed in percentage of specific anti-KMP11 CD8 T cells in the CD8 T cells population.
Figure 4:
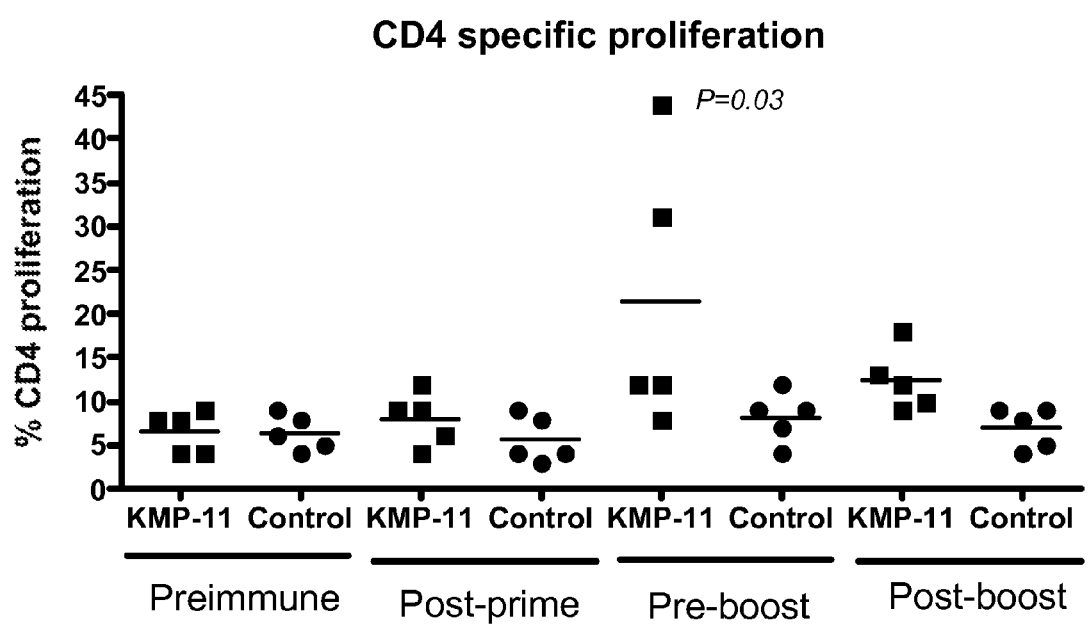
FIG. 4 shows the specific CD4 T cells proliferation before vaccination, between an initial vaccination and a subsequent boost vaccination, and after boost-vaccination; expressed in percentage of specific anti-KMP11 CD4 T cells in the CD4 T cells population.

At D1, D14, D41, D55 and D76, sera were analyzed for frequency of $CD8^+$ cells (see FIG. 1), frequency of interferon-γ-producing (IFN-γ) cells (see FIG. 2), specific CD8 T cell proliferation (see FIG. 3) and specific CD4 T cell proliferation (see FIG. 4).

IFN-γ Production by Cultured Whole Blood

The whole blood was diluted 1:8 in RPMI supplemented with 3% antibiotic/antimycotic solution (GIBCO, Grand Island, N.Y., USA) in a 48-well flat-bottomed culture plate with a final volume of 1 ml per well. Cells were stimulated by the addition of 25 µg/ml of soluble *L. infantum* extract (SLE) of Phorbol 12-myristate 13-acetate (PMA, Sigma-Aldrich Co., USA). After 48 h of incubation at 37° C., 700 µl of supernatant was removed from each well and stored at −20° C. until required for the cytokine assay. IFN-γ was measured using a capture ELISA assay for dogs (R&D Systems, Minneapolis, Minn., USA) following the manufacturer's instructions. Biotin-labeled detection antibodies were used, revealed with streptavidin-HRP (Amersham Biosciences) and TMB substrate (KPL, Gaithesburgh, Md., USA). The reaction was stopped by the addition of Stop solution (KPL) to each well. Absorbance values are read at 450 nm in an automatic micro-ELISA reader (Thermo Multiskan EX, Waltham, Mass., USA).

Cellular Profile of Peripheral Blood and Cytokine Staining

The phenotyping of peripheral blood cell populations was performed using whole blood samples collected at the indicated days. In short, 1 ml of blood was fixed and the erythrocytes lysed with fixative solution (10.0 g/l paraformaldehyde; 10.2 g/l cacodylic acid; 6.65 g/l sodium chloride; pH 7.2). After 10-min incubation, cells were washed twice with PBS—1% BSA buffer. Surface staining was carried out in a 96-well round bottomed microplate with anti-canine CD4-Alexa 647 and anti-canine CD8-PE. The data on fluorescently labeled cells were acquired in a FACSCALIBUR™ flow cytometer (Becton Dickinson, San Jose, Calif., USA). At least thirty thousand events were counted. Intracellular cytokine staining was carried out after permeabilization with saponin for the IFN-γ using anti-bovine IFN-γ-PE (Serotec).

Lymphoproliferation of Peripheral Blood Leukocytes (PBLs)

The lymphoproliferation assay was performed using PBLs obtained after separation with ficoll. PBMCs were diluted in 1 ml phosphate-buffered saline (PBS) and stained with the fluorescent dye carboxyfluorescein diacetate succinimidyl ester (CFSE, Molecular probes, Carlsbad, Calif., USA). After staining, cells were resuspended in 200 µl RPMI supplemented with 10% FBS and 3% antibiotic/antimycotic solution (GIBCO, Grand Island, N.Y., USA). All tests were performed in triplicate in 96-well flat-bottomed culture plates using SLE at a concentration of 25 μg/ml and Concanavalin A (ConA) (Sigma-Aldrich Co., USA) at 160 μg/ml. Incubation was carried out in a humidified 5% $CO_2$ atmosphere at 37° C. for 5 days. Cells were then collected and stained for CD4 or CD8 expression as described above. Percentage of proliferation was assessed by loss of fluorescent intensity in these populations.

Serological Analysis

Blood was collected at different time points, and the serum was separated and stored frozen at −20° C. Antigen-specific canine IgG, $IgG_1$ and $IgG_2$ were measured by indirect enzyme-linked immunosorbent assay (ELISA). Briefly, the antigens were coated onto 96-well microplates (MAX-ISORP™, Nalge Nunc, Rochester, N.Y., USA) at a concentration of 8 μg/ml for SLE and at 5 μg/ml for the recombinant antigens. Sera were added at the concentrations 1:100, 1:500 and three-fold serial dilutions thereafter followed by washes and addition of peroxidase-conjugated anti-dog IgG, $IgG_1$ and $IgG_2$ (Bethyl Laboratories Inc., Montgomery, Tex., USA) at 1:8000, 1:1500 and 1:3000 dilution, respectively. Wells were then washed and substrate and chromogen (TMB, KPL) were added and absorbance was read on an automatic ELISA microplate reader at 450 nm. The mean optical density of control canine sera was used as a baseline. The last serum dilution greater than three times above baseline was considered the titration endpoint. The geometric mean of these endpoints was calculated for the five dogs from each group.

Western Blot Analysis

Western blot analysis was performed using SLE (0.6 mg/ml), which were boiled in SDS sample buffer, separated on a 4-12% gradient Tris-Glycine SDS-PAGE gel (Invitrogen, Cal) and transferred onto a PVDF membrane (Pall Life Sciences, East Hills, N.Y.). The blot was blocked overnight with blocker solution (Invitrogen, Carlsbad, Calif., USA) and probed with each individual serum diluted 1:1000. Horseradish peroxidase-conjugated anti-dog was used as a secondary antibody at a dilution 1:2000. Development was performed with ECL reagent (Amersham Biosciences, Buckinghamshire, England) according to the manufacturer's instructions.

FIG. 1 shows a significant difference in the total of CD8 T cells present in the peripheral blood after the boost administration between the sera of the KMP11 vaccinated dogs and those of the control dogs (p=0.01).

Figure 2:
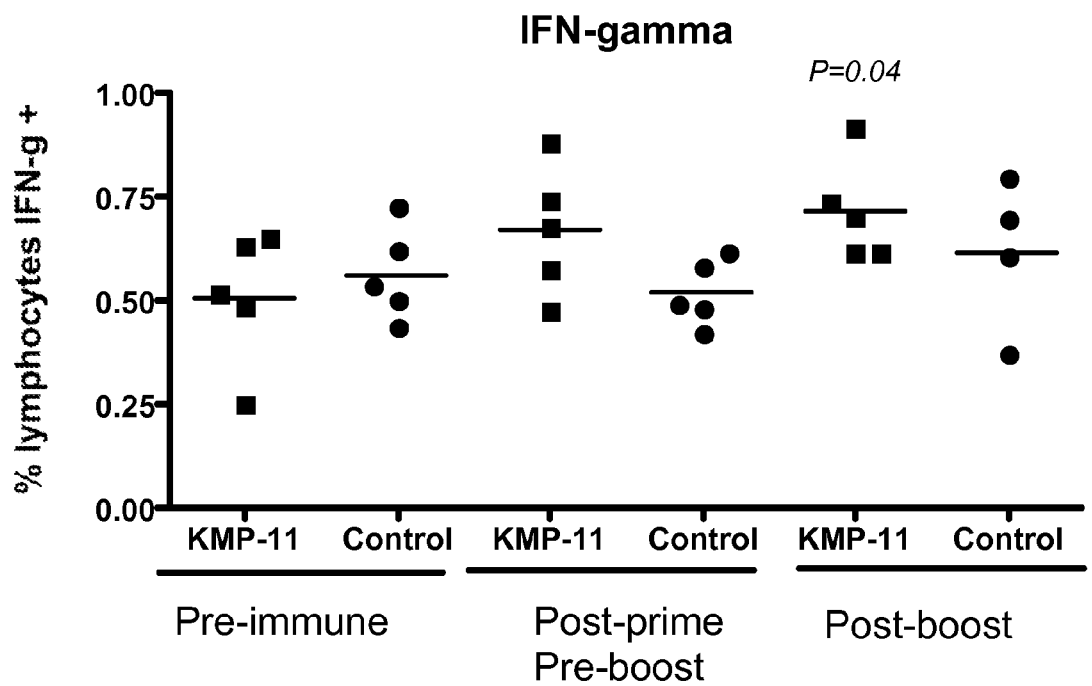
FIG. 2 shows the frequency of IFN-gamma-producing cells before vaccination, between an initial vaccination and a subsequent boost vaccination, and after boost-vaccination; expressed in percentage of IFN-gamma+ lymphocytes present in the peripheral blood.

The FIG. 2 shows a significant difference in the total of IFN-γ-producing cells present in the peripheral blood after the primo-administration and after the boost administration between the sera of the KMP11 vaccinated dogs and those of the control dogs (p=0.04).

FIG. 3 shows a significant difference in the total of specific anti-KMP11 CD8 T cells present in the peripheral blood before the boost administration (3 weeks after priming) and after the boost administration between the sera of the KMP11 vaccinated dogs and those of the control dogs (p=0.007).

FIG. 4 shows a significant difference in the total of specific anti-KMP11 CD4 T cells present in the peripheral blood before the boost administration (3 weeks after priming) and after the boost administration between the sera of the KMP11 vaccinated dogs and those of the control dogs (p=0.03).

Figure 5:
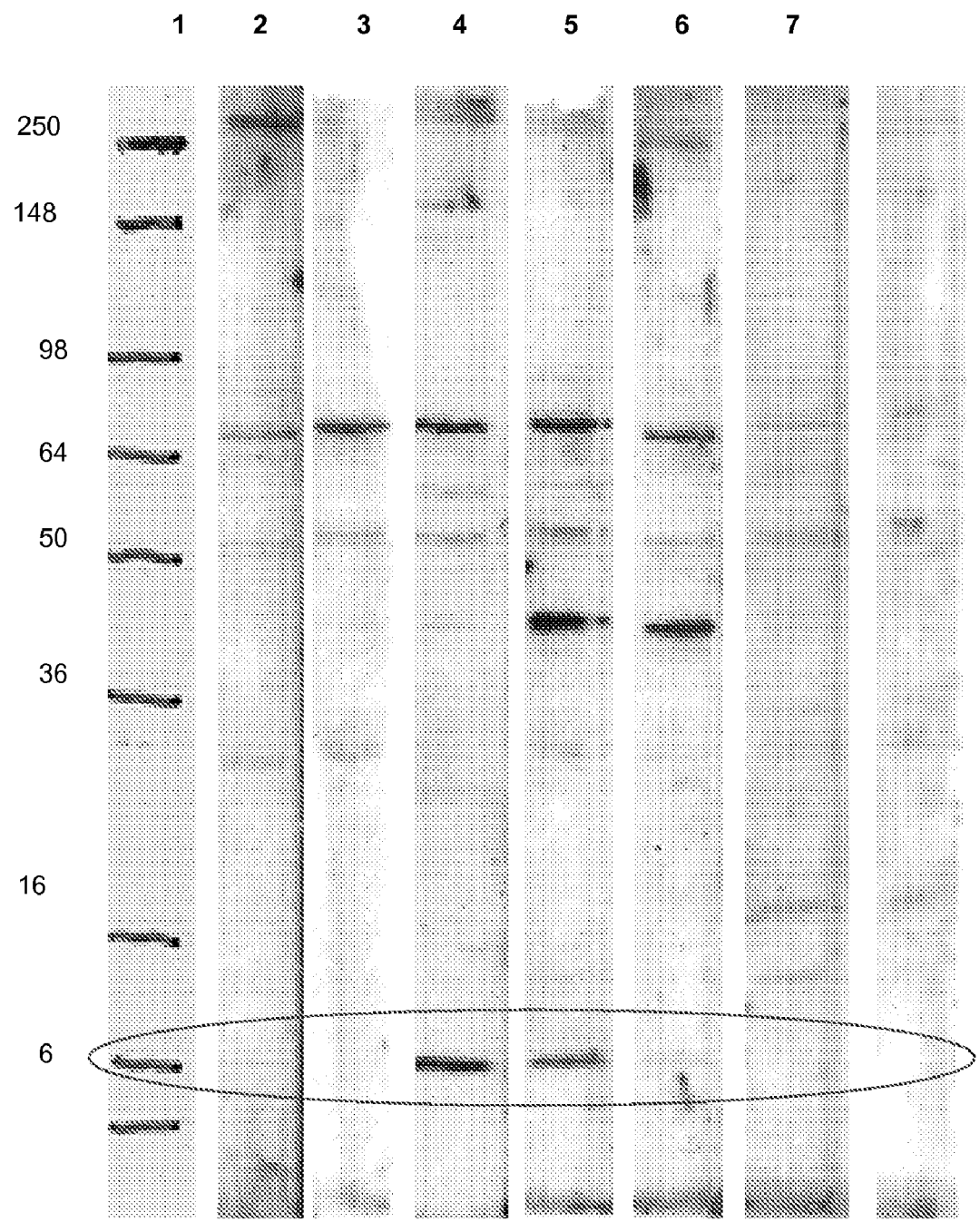
FIG. 5 is a Western Blot showing the IgG response of a KMP11 vaccinated dog, where column 1 is unvaccinated, column 2 is KMP11 vaccinated dog post-priming (D14), column 3 is KMP11 vaccinated dog post-boost (D41), column 4 is KMP11 vaccinated dog post-boost (D55), column 5 is KMP11 vaccinated dog post-boost (D76), column 6 is control dog post-priming (D14) and column 7 is control dog post-boost (D41). The study utilized *L. infantum* antigens 6 µg/10 µL, first antibodies (serum) 1/1000 and second antibodies (anti-dogs IgG-HRP) 1/2000.

At D0, D14, D41, D55 and D76, sera were also analyzed for antibody responses by Western Blot using *L. infantum* lysate at 6 μg/10 μl per lane (see FIG. 5). Sera were tested at a dilution of 1:1000. The secondary antibody was HRP anti-canine IgG reagent used at a dilution of 1:2000. The Western Blot results depicted in FIG. 5 show a clear post-boost KMP11-specific IgG response (see circled bands).

Example 3

Construction of an ALVAC Canarypox Virus Vector Expressing the *L. infantum* KMP11 Antigen The nucleotide insert used in the construction of vCP2350 was derived from the *L. infantum* KMP11 gene supplied by GeneArt GmbH (Regensburg, Germany). The nucleic acid sequence is synthetic with codon optimization for expression in mammalian cells (SEQ ID NO: 3). This nucleic acid sequence encodes *L. infantum* KMP11 antigen (SEQ ID NO: 4). Two different enzyme restriction sites flanked this nucleotide insert, an EcoRV site 5' of the coding region and a XbaI site 3' of the coding region.

To construct the ALVAC donor plasmid, pALVAC C5 H6p-*leishmania*-11 (pJSY1992.1), the nucleotide insert was digested using EcoRV/XbaI digestion in order to isolate the fragment comprising the synthetic KMP11 gene. (For discussion and examples of the plasmid, pALVAC, and the C5 locus, see e.g., U.S. Pat. Nos. 5,756,103; 5,833,975; and 6,780,407). The sequence of the vaccinia virus H6 promoter has been previously described (see e.g., Taylor et al. Vaccine. 6: 497-503, 1988a; Taylor et al. Vaccine. 6: 504-508, 1988b; Guo et al. J Virol 63: 4189-4198, 1989).

Figure 6:
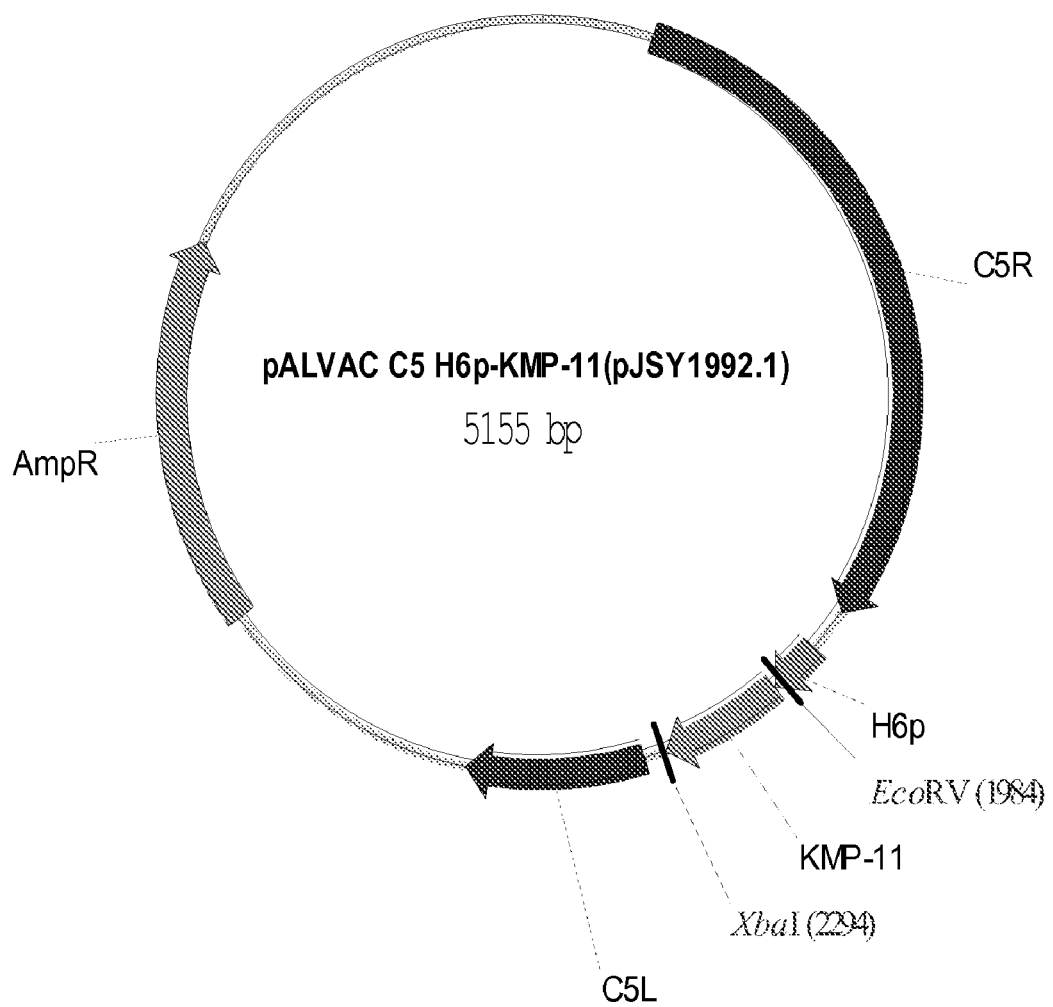
FIG. 6 is the plasmid diagram of the ALVAC donor plasmid pJSY1992.1.

This fragment was then ligated to EcoRV/XbaI digested pALVAC C5 H6p donor (pCXL148.2). The resulting plasmid pJSY1992.1 (FIG. 6) was sequenced (SEQ ID NO: 6) and confirmed to contain the correct nucleic acid sequence (SEQ ID NO: 3) of the KMP11 gene.

To generate vCP2350, plasmid pJSY1992.1, which contained the synthetic KMP11 gene, was linearized with NotI restriction enzyme. The linearized fragments were individually transfected into ALVAC-infected primary CEF cells by using the calcium phosphate precipitation method described previously (Panicali et al., Proc. Natl Acad Sci USA, 1982, 79: 4927-4931; Piccini et al., Methods Enzymol., 1987, 153: 545-563). After 24 h, the transfected cells were harvested, sonicated and used for recombinant virus screening.

Recombinant plaques were screened based on the plaque lift hybridization method using a *Leishmania* synthetic KMP11-specific probe which was labeled with horse radish peroxidase according to the manufacturer's protocol (Amersham Cat# RPN-3001). After three sequential rounds of plaque purification, the recombinants, designated as vCP2350.1.1.5, were generated and confirmed by hybridization as 100% positive for the *Leishmania* synthetic KMP11 insert and 100% negative for the C5 ORF.

A single plaque was selected from the third round of plaque purification and expanded to obtain P1 (60 mm), P2 (T75 flasks), P3 (roller bottles) stocks to amplify vCP2350.1.1.5. The infected cell culture fluid from the roller bottles was harvested and concentrated to produce virus stock (about 3.5 mL at $1.3 \times 10^{10}$ PFU/mL).

Figure 7:
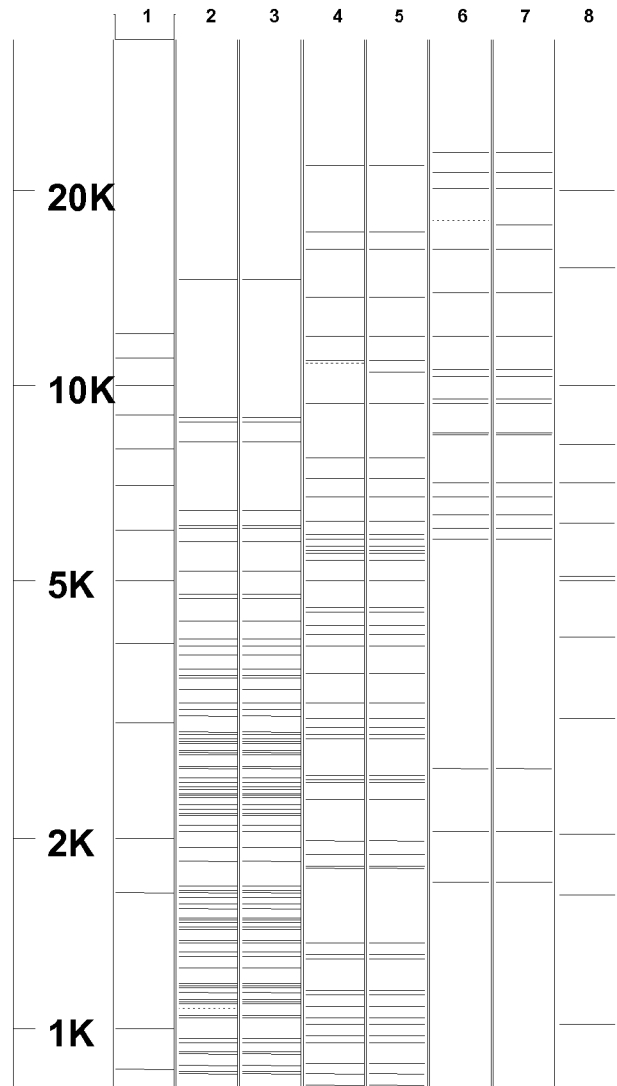
FIG. 7 shows a theoretical restriction enzyme gel for the genomic DNA of vCP2350.1.1.5, created in Vector NTI.
Figure 8:
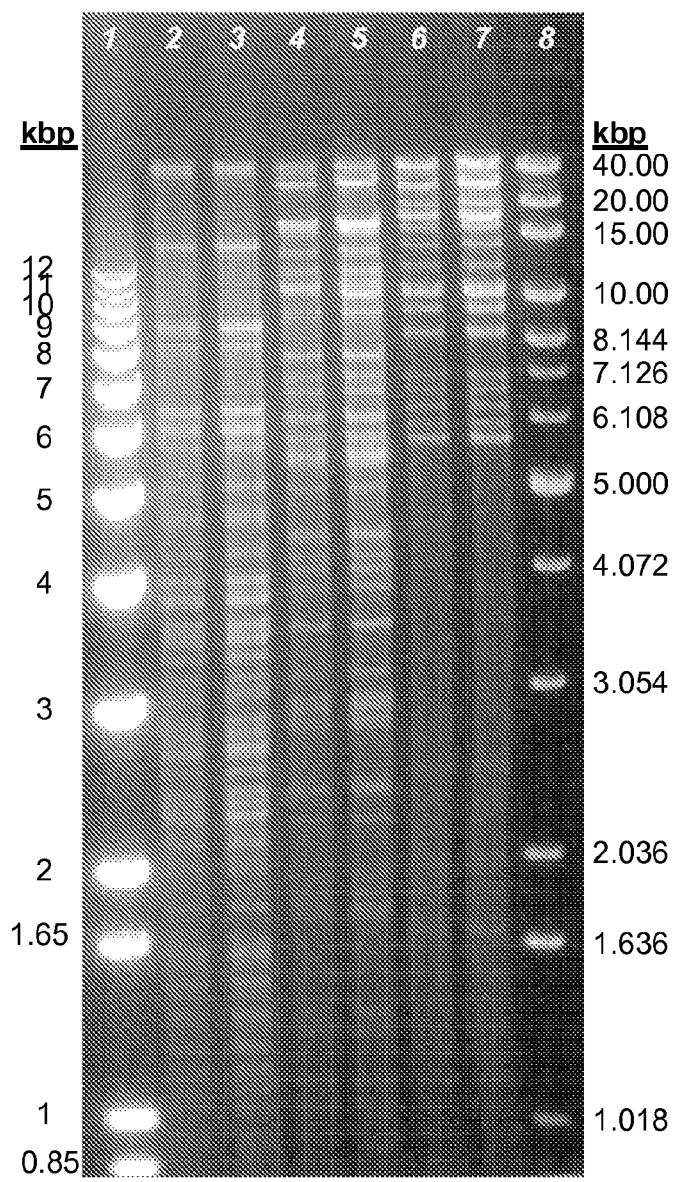
FIG. 8 is a restriction analysis gel of vCP2350.1.1.5 after digestion with BglII, HindIII and PstI, and separation by 0.8% agarose gel electrophoresis.

A theoretical restriction enzyme gel for the genomic DNA was created in Vector NTI and is shown in FIG. 7. Genomic DNA was extracted from vCP2350.1.1.5 and digested with BglII, HindIII and PstI, and separated by 0.8% agarose gel electrophoresis. The results showed the correct insertion of the foreign gene sequence (see FIG. 8).

Figure 9:
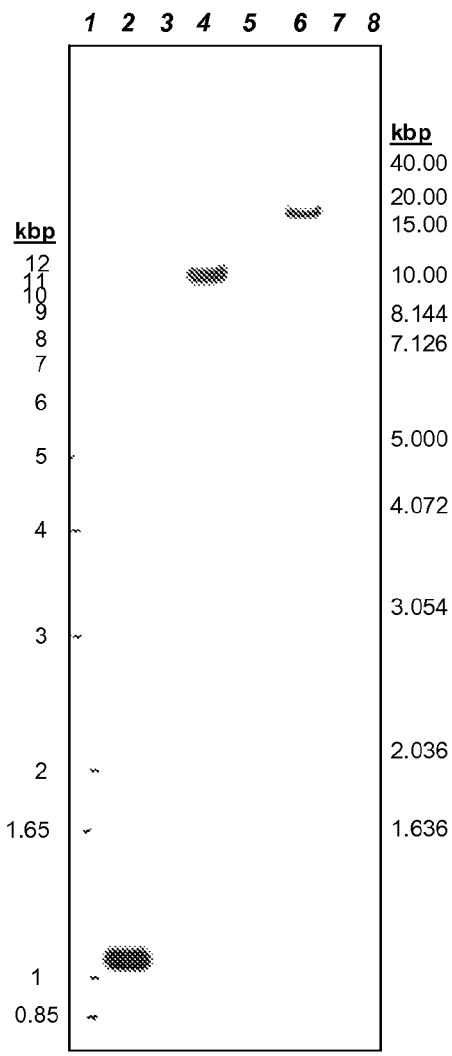
FIG. 9 is a Southern blot analysis of vCP2350.1.1.5 obtained by probing with *Leishmania* synthetic KMP11 probe.

The genomic DNA digested with BglII, HindIII and PstI was transferred to nylon membrane and Southern blot analysis was performed by probing with *Leishmania* synthetic KMP11 probe. Bands were observed at the expected sizes, indicating the correct insertion of *Leishmania* synthetic KMP11 into the C5 locus (FIG. 9).

A more detailed analysis of the P3 stock genomic DNA was performed by PCR amplification and sequence analysis of the flanking arms of the C5 locus and the *Leishmania* synthetic KMP11 insert. Primers 7931.DC (SEQ ID NO: 7) and 7932.DC (SEQ ID NO: 8) located beyond the arms of the C5 locus were used to amplify the entire C5R-*Leishmania* synthetic KMP11 insert-C5L fragment. The results showed that the sequence of the *Leishmania* synthetic KMP11 insert and the C5 left and right arms around the *Leishmania* synthetic KMP11 insert in vCP2350.1.1.5 were correct.

Recombinant vectors in accordance with the present invention can therefore comprise a recombinant avipox virus, eg canarypox virus vector, such as a recombinant ALVAC vector, having a promoter for driving expression, for example the H6 promoter, operably linked to DNA encoding KMP11, in a suitable site in the avipox virus genome such as the C3 or C5 locus of canarypox (eg ALVAC).

Example 4

Prime-boost Vaccination of Dogs Against Leishmaniasis with Plasmid-based Vaccines and ALVAC Canarypox Virus Vector-based Vaccines At week 17 after the primo-administration, the animals of the vaccinated group of Example 2 were administered the ALVAC canarypox virus vCP2350 vector vaccine of Example 3 in a volume of 0.2 ml of TE pH 8 buffer (i.e., 2 mg/ml).

At the same time, the animals of the control group of Example 2 were administered a vaccine comprising a control ALVAC canarypox virus vector expressing a CDV antigen (vCP258, see Example 19 of U.S. Pat. No. 5,756,102) in a volume of 0.2 ml of TE pH 8 buffer (i.e., 2 mg/ml).

The dose of vaccine, vCP2350 vector vaccine for vaccinated animals and vCP258 vector vaccine for control animals, was $10^8$ PFU per animal. The administration was performed for each animal intradermally in the right medial thigh using the MERIAL VETJET™ needle free injector. The inner thigh area was clipped free of fur and disinfected with povidone iodine (VETEDINE®, Vetoquinol, Lure, France) before administration.

Sera of animals are collected and analyzed for frequency of $CD8^+$ cells, frequency of IFN-γ-producing cells, specific CD8 T cell proliferation and specific CD4 T cell proliferation as described in Example 2.

A challenge with *L. infantum* amastigotes is scheduled at week 22 after the primo-administration.

The invention will now be further described by the following numbered paragraphs:

1. Use of in vivo expression vectors in a prime-boost administration regimen, comprising a primo-administration of a vaccine comprising, in a pharmaceutically acceptable vehicle, diluent or excipient, an in vivo expression vector containing a polynucleotide sequence for expressing, in vivo, *Leishmania* KMP11 polypeptide, antigen, epitope or immunogen, followed by a boost administration of a vaccine comprising, in a pharmaceutically acceptable vehicle or excipient, an in vivo expression vector containing a polynucleotide sequence for expressing, in vivo, *Leishmania* KMP11 antigen, epitope or immunogen to protect canine animals from leishmaniasis and/or to prevent disease progression in infected canine animals.

2. The use according to the paragraph 1, wherein the protection is shown by the prevention of the diffusion and implantation of the parasite into internal organs of said canine animals.

3. The use according to the paragraph 1 for the production of a vaccine for the induction of humoral immune response in canine animals against KMP11.

4. The use according to the paragraph 3, wherein the induction in canine animals is induction of anti-KMP11 IgG1.

5. The use according to any one of the paragraphs 1 to 4 for the production of a vaccine for the induction of cell-mediated immune response in canine animals against KMP11.

6. The use according to the paragraph 5, wherein the induction in canine animals is induction of CD8 T cell-mediated immune response against KMP11.

7. The use according to the paragraph 5 or 6, wherein the induction in canine animals is induction of CD4 T cell-mediated immune response against KMP11.

8. The use according to any one of the paragraphs 1 to 7, wherein the in vivo expression vector for the primo-administration is a plasmid, and the in vivo expression vector for the boost administration is a recombinant viral vector.

9. The use according to the paragraph 8, wherein the in vivo expression vector for the primo-administration is a plasmid, and the in vivo expression vector for the boost administration is a recombinant canarypox virus vector.

10. The use according to the paragraph 9, wherein the in vivo expression vector for the primo-administration is the plasmid pVR1020 KMP11, and the in vivo expression vector for the boost administration is a recombinant canarypox virus vector vCP2350.

11. The use according to any one of the paragraphs 1 to 10, wherein the polynucleotide sequence encoding the *Leishmania* KMP11 is the codon-optimized polynucleotide sequence SEQ ID No3, encoding a *Leishmania infantum* KMP11 antigen SEQ ID No4.

12. The use according to any one of the paragraphs 1 to 11, wherein the primo-administration is coupled to electrotransfer treatment.

13. The use according to any one of the paragraphs 1 to 7, wherein the in vivo expression vectors for primo-administration and for boost administration are plasmids and comprise a polynucleotide sequence encoding a *Leishmania* KMP11 antigen or immunogen or an epitope thereof, and the primo-administration is done intradermally with a needle free apparatus and the boost administration is done intramuscularly with a syringe and a needle and coupled to electrotransfer treatment.

14. The use according to any one of the paragraphs 1 to 7, wherein the in vivo expression vectors for primo-administration and for boost administration are plasmids and comprise a polynucleotide sequence encoding a *Leishmania* KMP11 antigen or immunogen or an epitope thereof, and the primo-administration is done intramuscularly with a syringe and a needle and coupled to electrotransfer treatment and the boost administration is done intradermally with a needle free apparatus.

15. The use according to the paragraph 13 or 14, wherein the in vivo expression vectors are the plasmid pVR1020 KMP11.

16. The use according to the paragraph 13 or 14, wherein the polynucleotide sequence encoding the *Leishmania* KMP11 is the codon-optimized polynucleotide sequence SEQ ID No3, encoding a *Leishmania* infantum KMP11 antigen SEQ ID No4.

17. A kit for prime-boost administration regimen according to any one of the paragraphs 1 to 12, comprising at least two vials, one vial containing a vaccine for the primo-vaccination, the other(s) vial(s) containing a vaccine for the boost-vaccination.

18. The kit according to the paragraph 17, wherein the kit comprises two vials, one containing a plasmid-based vaccine for the primo-vaccination, the other vial containing a recombinant viral vector-based vaccine for the boost-vaccination.

The invention claimed is:

1. A recombinant vector that contains and expresses in vivo a nucleic acid sequence comprising the sequence of SEQ ID NO:3 encoding *Leishmania infantum* KMP11 polypeptide which is operatively linked to a promoter that elicits an immune response in a dog against Leishmania.

2. The recombinant vector according to claim 1, wherein the *Leishmania infantum* KMP11 polypeptide comprises the amino acid sequence of SEQ ID NO:4.

3. A recombinant vector comprising a polynucleotide encoding a KMP11 protein comprising the sequence of SEQ ID NO:4.

4. The recombinant vector according to claim 1 or claim 3, wherein the vector is a plasmid selected from the group consisting of pVR1020 and pVR1012.

5. The recombinant vector according to claim 4, wherein the promoter is selected from the group consisting of human or murine cytomegalovirus major immediate early (IE) promoter (CMV-IE), the early/late promoter of the SV40 virus, and the LTR promoter of the Rous sarcoma virus.

6. The recombinant vector according to claim 1 or claim 3, wherein the vector is a recombinant viral vector.

7. The recombinant vector according to claim 6, wherein the recombinant viral vector is selected from the group consisting of poxvirus, adenovirus and herpesvirus.

8. The recombinant vector according to claim 7, wherein the recombinant viral vector is an avipox virus.

9. The recombinant vector according to claim 8, wherein the avipox virus is fowlpox or canarypox.

10. The recombinant vector according to claim 9, wherein the canarypox vector is an ALVAC.

11. The recombinant vector according to claim 9, wherein the fowlpox vector is a TROVAC.

12. A pharmaceutical composition comprising the recombinant vector of claim 1 or claim 3 and a pharmaceutically acceptable vehicle, diluent or excipient.

13. The pharmaceutical composition according to claim 12, wherein the composition is administered to an animal in a prime-boost regimen.

* * * * *

SEQUENCE LISTING

<160> NUMBER OF SEQ ID NOS: 8

<210> SEQ ID NO 1
<211> LENGTH: 279
<212> TYPE: DNA
<213> ORGANISM: Leishmania infantum

<400> SEQUENCE: 1

```
atggccacca cgtacgagga gttctcggcg aagttggacc gcctggatga ggagttcaac      60
aggaagatgc aggaacagaa cgccaagttc tttgccgaca agccggatga gtcgacgctg     120
tcgcccgaga tgaaggagca ctacgagaag ttcgagcgca tgatcaagga gcacacagag     180
aagttcaaca agaagatgca cgagcactcg gagcacttca agcagaagtt cgctgagctg     240
ctcgagcagc agaaggctgc gcagtaccca tccaagtaa                            279
```

<210> SEQ ID NO 2
<211> LENGTH: 92
<212> TYPE: PRT
<213> ORGANISM: Leishmania infantum

<400> SEQUENCE: 2

```
Met Ala Thr Thr Tyr Glu Glu Phe Ser Ala Lys Leu Asp Arg Leu Asp
 1               5                  10                  15

Glu Glu Phe Asn Arg Lys Met Gln Glu Gln Asn Ala Lys Phe Phe Ala
            20                  25                  30

Asp Lys Pro Asp Glu Ser Thr Leu Ser Pro Glu Met Lys Glu His Tyr
        35                  40                  45

Glu Lys Phe Glu Arg Met Ile Lys Glu His Thr Glu Lys Phe Asn Lys
    50                  55                  60

Lys Met His Glu His Ser Glu His Phe Lys Gln Lys Phe Ala Glu Leu
65                  70                  75                  80

Leu Glu Gln Gln Lys Ala Ala Gln Tyr Pro Ser Lys
                85                  90
```

<210> SEQ ID NO 3
<211> LENGTH: 279
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
atggccacca cctacgagga attcagcgcc aagctggacc ggctggacga agagttcaac      60
cggaagatgc aggaacagaa cgccaagttc ttcgccgaca agcccgacga gagcaccctg     120
agccccgaga tgaaagagca ctacgagaag ttcgagcgga tgatccggga gcacaccgag     180
aagtttaaca agaagatgca cgagcacagc gagcacttca agcagaagtt cgccgagctg     240
ctggaacagc agaaggccgc ccagtacccc agcaagtga                            279
```

<210> SEQ ID NO 4
<211> LENGTH: 92
<212> TYPE: PRT
<213> ORGANISM: Leishmania infantum

<400> SEQUENCE: 4

```
Met Ala Thr Thr Tyr Glu Glu Phe Ser Ala Lys Leu Asp Arg Leu Asp
 1               5                  10                  15
```

```
Glu Glu Phe Asn Arg Lys Met Gln Glu Gln Asn Ala Lys Phe Phe Ala
             20                  25                  30

Asp Lys Pro Asp Glu Ser Thr Leu Ser Pro Glu Met Lys Glu His Tyr
         35                  40                  45

Glu Lys Phe Glu Arg Met Ile Arg Glu His Thr Glu Lys Phe Asn Lys
     50                  55                  60

Lys Met His Glu His Ser Glu His Phe Lys Gln Lys Phe Ala Glu Leu
 65                  70                  75                  80

Leu Glu Gln Gln Lys Ala Ala Gln Tyr Pro Ser Lys
                 85                  90

<210> SEQ ID NO 5
<211> LENGTH: 5338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
```

| | | | | | |
|---|---|---|---|---|---|
| aagggatcca | gatctgctgt | gccttctagt | tgccagccat | ctgttgtttg | ccctcccccc | 60 |
| gtgccttcct | tgaccctgga | aggtgccact | cccactgtcc | tttcctaata | aaatgaggaa | 120 |
| attgcatcgc | attgtctgag | taggtgtcat | tctattctgg | ggggtggggt | ggggcagcac | 180 |
| agcaagggg | aggattggga | agacaatagc | aggcatgctg | gggatgcggt | gggctctatg | 240 |
| ggtacccagg | tgctgaagaa | ttgacccggt | tcctcctggg | ccagaaagaa | gcaggcacat | 300 |
| ccccttctct | gtgacacacc | ctgtccacgc | ccctggttct | tagttccagc | cccactcata | 360 |
| ggacactcat | agctcaggag | ggctccgcct | tcaatcccac | ccgctaaagt | acttggagcg | 420 |
| gtctctccct | ccctcatcag | cccaccaaac | caaacctagc | ctccaagagt | gggaagaaat | 480 |
| taaagcaaga | taggctatta | agtgcagagg | gagagaaaat | gcctccaaca | tgtgaggaag | 540 |
| taatgagaga | aatcatagaa | tttcttccgc | ttcctcgctc | actgactcgc | tgcgctcggt | 600 |
| cgttcggctg | cggcgagcgg | tatcagctca | ctcaaaggcg | gtaatacggt | tatccacaga | 660 |
| atcaggggat | aacgcaggaa | agaacatgtg | agcaaaaggc | cagcaaaagg | ccaggaaccg | 720 |
| taaaaaggcc | gcgttgctgg | cgttttttcca | taggctccgc | cccctgacg | agcatcacaa | 780 |
| aaatcgacgc | tcaagtcaga | ggtggcgaaa | cccgacagga | ctataaagat | accaggcgtt | 840 |
| tccccctgga | agctccctcg | tgcgctctcc | tgttccgacc | ctgccgctta | ccggatacct | 900 |
| gtccgccttt | ctcccttcgg | gaagcgtggc | gctttctcaa | tgctcacgct | gtaggtatct | 960 |
| cagttcggtg | taggtcgttc | gctccaagct | gggctgtgtg | cacgaacccc | ccgttcagcc | 1020 |
| cgaccgctgc | gccttatccg | gtaactatcg | tcttgagtcc | aacccggtaa | gacacgactt | 1080 |
| atcgccactg | gcagcagcca | ctggtaacag | gattagcaga | gcgaggtatg | taggcggtgc | 1140 |
| tacagagttc | ttgaagtggt | ggcctaacta | cggctacact | agaaggacag | tatttggtat | 1200 |
| ctgcgctctg | ctgaagccag | ttaccttcgg | aaaaagagtt | ggtagctctt | gatccggcaa | 1260 |
| acaaaccacc | gctggtagcg | gtggtttttt | tgtttgcaag | cagcagatta | cgcgcagaaa | 1320 |
| aaaaggatct | caagaagatc | ctttgatctt | ttctacgggg | tctgacgctc | agtggaacga | 1380 |
| aaactcacgt | taagggattt | tggtcatgag | attatcaaaa | aggatcttca | cctagatcct | 1440 |
| tttaaattaa | aaatgaagtt | ttaaatcaat | ctaaagtata | tatgagtaaa | cttggtctga | 1500 |
| cagttaccaa | tgcttaatca | gtgaggcacc | tatctcagcg | atctgtctat | ttcgttcatc | 1560 |

```
catagttgcc tgactccggg ggggggggc gctgaggtct gcctcgtgaa aaggtgttg      1620
ctgactcata ccaggcctga atcgccccat catccagcca gaaagtgagg gagccacggt   1680
tgatgagagc tttgttgtag gtggaccagt tggtgatttt gaacttttgc tttgccacgg   1740
aacggtctgc gttgtcggga agatgcgtga tctgatcctt caactcagca aaagttcgat   1800
ttattcaaca aagccgccgt cccgtcaagt cagcgtaatg ctctgccagt gttacaacca   1860
attaaccaat tctgattaga aaactcatc gagcatcaaa tgaaactgca atttattcat    1920
atcaggatta tcaataccat attttttgaaa aagccgtttc tgtaatgaag gagaaaactc  1980
accgaggcag ttccatagga tggcaagatc ctggtatcgg tctgcgattc cgactcgtcc   2040
aacatcaata caacctatta atttcccctc gtcaaaaata aggttatcaa gtgagaaatc   2100
accatgagtg acgactgaat ccggtgagaa tggcaaaagc ttatgcattt ctttccagac   2160
ttgttcaaca ggccagccat tacgctcgtc atcaaaatca ctcgcatcaa ccaaaccgtt   2220
attcattcgt gattgcgcct gagcgagacg aaatacgcga tcgctgttaa aaggacaatt   2280
acaaacagga atcgaatgca accggcgcag gaacactgcc agcgcatcaa caatattttc   2340
acctgaatca ggatattctt ctaatacctg gaatgctgtt ttcccgggga tcgcagtggt   2400
gagtaaccat gcatcatcag gagtacggat aaaatgcttg atggtcggaa gaggcataaa   2460
ttccgtcagc cagtttagtc tgaccatctc atctgtaaca tcattggcaa cgctaccttt   2520
gccatgtttc agaaacaact ctggcgcatc gggcttccca tacaatcgat agattgtcgc   2580
acctgattgc ccgacattat cgcgagccca tttataccca tataaatcag catccatgtt   2640
ggaatttaat cgcggcctcg agcaagacgt ttcccgttga atatggctca taacacccct   2700
tgtattactg tttatgtaag cagacagttt tattgttcat gatgatatat ttttatcttg   2760
tgcaatgtaa catcagagat tttgagacac aacgtggctt tccccccccc cccattattg   2820
aagcatttat cagggttatt gtctcatgag cggatacata tttgaatgta tttagaaaaa   2880
taaacaaata ggggttccgc gcacatttcc ccgaaaagtg ccacctgacg tctaagaaac   2940
cattattatc atgacattaa cctataaaaa taggcgtatc acgaggccct ttcgtctcgc   3000
gcgtttcggt gatgacggtg aaaacctctg acacatgcag ctcccggaga cggtcacagc   3060
ttgtctgtaa gcggatgccg ggagcagaca agcccgtcag ggcgcgtcag cgggtgttgg   3120
cgggtgtcgg gctggctta actatgcggc atcagagcag attgtactga gagtgcacca   3180
tatgcggtgt gaaataccgc acagatgcgt aaggagaaaa taccgcatca gattggctat   3240
tggccattgc atacgttgta tccatatcat aatatgtaca tttatattgg ctcatgtcca   3300
acattaccgc catgttgaca ttgattattg actagttatt aatagtaatc aattacgggg   3360
tcattagttc atagcccata tatggagttc cgcgttacat aacttacggt aaatggcccg   3420
cctggctgac cgcccaacga cccccgccca ttgacgtcaa taatgacgta tgttcccata   3480
gtaacgccaa tagggacttt ccattgacgt caatgggtgg agtatttacg gtaaactgcc   3540
cacttggcag tacatcaagt gtatcatatg ccaagtacgc ccctattga cgtcaatgac    3600
ggtaaatggc ccgcctggca ttatgcccag tacatgacct tatgggactt tcctacttgg   3660
cagtacatct acgtattagt catcgctatt accatggtga tgcggttttg gcagtacatc   3720
aatgggcgtg gatagcggtt tgactcacgg ggatttccaa gtctccaccc cattgacgtc   3780
aatgggagtt gttttggca ccaaaatcaa cgggactttc caaaatgtcg taacaactcc    3840
gccccattga cgcaaatggg cggtaggcgt gtacggtggg aggtctatat aagcagagct   3900
cgtttagtga accgtcagat cgcctggaga cgccatccac gctgttttga cctccataga   3960
```

```
agacaccggg accgatccag cctccgcggc cgggaacggt gcattggaac gcggattccc    4020
cgtgccaaga gtgacgtaag taccgcctat agagtctata ggcccacccc cttggcttct    4080
tatgcatgct atactgtttt tggcttgggg tctatacacc cccgcttcct catgttatag    4140
gtgatggtat agcttagcct ataggtgtgg gttattgacc attattgacc actccctat     4200 tggtgacgat actttccatt actaatccat aacatggctc tttgccacaa ctctctttat    4260
tggctatatg ccaatacact gtccttcaga gactgacacg gactctgtat ttttacagga    4320
tggggtctca tttattattt acaaattcac atatacaaca ccaccgtccc cagtgcccgc    4380
agtttttatt aaacataacg tgggatctcc acgcgaatct cgggtacgtg ttccggacat    4440
gggctcttct ccggtagcgg cggagcttct acatccgagc cctgctccca tgcctccagc    4500
gactcatggt cgctcggcag ctccttgctc ctaacagtgg aggccagact taggcacagc    4560
acgatgccca ccaccaccag tgtgccgcac aaggccgtgg cggtagggta tgtgtctgaa    4620
aatgagctcg gggagcgggc ttgcaccgct gacgcatttg aagacttaa ggcagcggca     4680 gaagaagatg caggcagctg agttgttgtg ttctgataag agtcagaggt aactcccgtt    4740
gcggtgctgt taacggtgga gggcagtgta gtctgagcag tactcgttgc tgccgcgcgc    4800
gccaccagac ataatagctg acagactaac agactgttcc tttccatggg tcttttctca    4860
cgtcaccgtc gtcgaccaga gctgagatcc tacaggagtc cagggctgga gagaaaacct    4920
ctgcgaggaa agggaaggag caagccgtga atttaaggga cgctgtgaag caatcatgga    4980
tgcaatgaag agagggctct gctgtgtgct gctgctgtgt ggagcagtct tcgtttcgcc    5040
cagcggtacc ggatccctta tggccaccac gtacgaggag ttctcggcga agttggaccg    5100
cctggatgag gagttcaaca ggaagatgca ggaacagaac gccaagttct ttgcggacaa    5160
gccggatgag tcgacgctgt cgcccgagat gaaggagcac tacgagaagt cgagcgcat     5220 gatcaaggag cacacagaga agttcaacaa gaagatgcac gagcactcgg agcacttcaa    5280
gcagaagttc gctgagctgc tcgagcagca aaggctgcg cagtacccat ccaagtaa      5338
```

<210> SEQ ID NO 6
<211> LENGTH: 5155
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
gcgcccaata cgcaaaccgc ctctccccgc gcgttggccg attcattaat gcagctggca      60
cgacaggttt cccgactgga aagcgggcag tgagcgcaac gcaattaatg tgagttagct     120
cactcattag gcaccccagg ctttacactt tatgcttccg gctcgtatgt tgtgtggaat     180
tgtgagcgga taacaatttc acacaggaaa cagctatgac catgattacg aattgcggcc     240
gcaattctga atgttaaatg ttatactttg gatgaagcta taaatatgca ttggaaaaat     300
aatccattta agaaaggat tcaaatacta caaaacctaa gcgataatat gttaactaag      360
cttattctta acgacgcttt aaatatacac aaataaacat aattttgta taacctaaca     420 ataactaaa acataaaaat aataaaagga aatgtaatat cgtaattatt ttactcagga     480
atggggttaa atatttatat cacgtgtata tctatactgt tatcgtatac tctttacaat    540
tactattacg aatatgcaag agataataag attacgtatt taagagaatc ttgtcatgat    600
aattgggtac gacatagtga taaatgctat ttcgcatcgt tacataaagt cagttggaaa    660
```

```
gatggatttg acagatgtaa cttaataggt gcaaaaatgt taaataacag cattctatcg      720
gaagatagga taccagttat attatacaaa aatcactggt tggataaaac agattctgca      780
atattcgtaa aagatgaaga ttactgcgaa tttgtaaact atgacaataa aaagccattt      840
atctcaacga catcgtgtaa ttcttccatg ttttatgtat gtgtttcaga tattatgaga      900
ttactataaa cttttgtat acttatattc cgtaaactat attaatcatg aagaaaatga       960
aaaagtatag aagctgttca cgagcggttg ttgaaaacaa caaaattata cattcaagat     1020
ggcttacata tacgtctgtg aggctatcat ggataatgac aatgcatctc taaataggtt     1080
tttggacaat ggattcgacc ctaacacgga atatggtact ctacaatctc ctcttgaaat     1140
ggctgtaatg ttcaagaata ccgaggctat aaaaatcttg atgaggtatg agctaaacc      1200 tgtagttact gaatgcacaa cttcttgtct gcatgatgcg gtgttgagag acgactacaa     1260
aatagtgaaa gatctgttga agaataacta tgtaaacaat gttctttaca gcggaggctt     1320
tactcctttg tgtttggcag cttaccttaa caaagttaat ttggttaaac ttctattggc     1380
tcattcggcg gatgtagata tttcaaacac ggatcggtta actcctctac atatagccgt     1440
atcaaataaa aatttaacaa tggttaaact tctattgaac aaaggtgctg atactgactt     1500
gctggataac atgggacgta ctcctttaat gatcgctgta caatctggaa atattgaaat     1560
atgtagcaca ctacttaaaa aaaataaaat gtccagaact gggaaaaatt gatcttgcca     1620
gctgtaattc atggtagaaa agaagtgctc aggctacttt tcaacaaagg agcagatgta     1680
aactacatct ttgaaagaaa tggaaaatca tatactgttt tggaattgat taagaaagt      1740 tactctgaga cacaaaagag gtagctgaag tggtactctc aaaggtacgt gactaattag     1800
ctataaaaag gatccgggtt aattaattag tcatcaggca gggcgagaac gagactatct     1860
gctcgttaat taattagagc ttctttattc tatacttaaa aagtgaaaat aaatacaaag     1920
gttcttgagg gttgtgttaa attgaaagcg agaaataatc ataaattatt tcattatcgc     1980
gatatccgtt aagtttgtat cgtaatggcc accacctacg aggaattcag cgccaagctg     2040
gaccggctgg acgaagagtt caaccggaag atgcaggaac agaacgccaa gttcttcgcc     2100
gacaagcccg acgagagcac cctgagcccc gagatgaaag agcactacga agttcgag       2160 cggatgatcc gggagcacac cgagaagttt aacaagaaga tgcacgagca gcgcgagcac     2220
ttcaagcaga agttcgccga gctgctggaa cagcagaagg ccgcccagta ccccagcaag     2280
tgatgaggat cctctagaat cgatcccggg ttttatgac tagttaatca cggccgctta      2340
taaagatcta aaatgcataa tttctaaata atgaaaaaa gtacatcatg agcaacgcgt       2400
tagtatattt tacaatggag attaacgctc tataccgttc tatgtttatt gattcagatg     2460 atgtttaga aaagaaagtt attgaatatg aaaactttaa tgaagatgaa gatgacgacg       2520
atgattattg ttgtaaatct gttttagatg aagaagatga cgcgctaaag tatactatgg     2580
ttacaaagta taagtctata ctactaatgg cgacttgtgc aagaaggtat agtatagtga     2640
aaatgttgtt agattatgat tatgaaaaac caaataaatc agatccatat ctaaaggtat     2700 ctccttttgca cataatttca tctattccta gtttagaata cctgcagcca agcttggcac    2760
tggccgtcgt tttacaacgt cgtgactggg aaaaccctgg cgttacccaa cttaatcgcc     2820
ttgcagcaca tccccctttc gccagctggc gtaatagcga agaggcccgc accgatcgcc     2880
cttcccaaca gttgcgcagc ctgaatggcg aatggcgcct gatgcggtat tttctcctta     2940
cgcatctgtg cggtatttca caccgcatat ggtgcactct cagtacaatc tgctctgatg     3000
```

-continued

```
ccgcatagtt aagccagccc cgacacccgc caacacccgc tgacgcgccc tgacgggctt    3060
gtctgctccc ggcatccgct tacagacaag ctgtgaccgt ctccgggagc tgcatgtgtc    3120
agaggttttc accgtcatca ccgaaacgcg cgagacgaaa gggcctcgtg atacgcctat    3180
ttttataggt taatgtcatg ataataatgg tttcttagac gtcaggtggc acttttcggg    3240
gaaatgtgcg cggaacccct atttgtttat ttttctaaat acattcaaat atgtatccgc    3300
tcatgagaca ataaccctga taaatgcttc aataatattg aaaaggaag agtatgagta     3360 ttcaacattt ccgtgtcgcc cttattccct tttttgcggc attttgcctt cctgttttg     3420 ctcacccaga aacgctggtg aaagtaaaag atgctgaaga tcagttgggt gcacgagtgg    3480
gttacatcga actggatctc aacagcggta agatccttga gttttcgc cccgaagaac      3540 gttttccaat gatgagcact tttaaagttc tgctatgtgg cgcggtatta tcccgtattg    3600
acgccgggca agagcaactc ggtcgccgca tacactattc tcagaatgac ttggttgagt    3660
actcaccagt cacagaaaag catcttacgg atggcatgac agtaagagaa ttatgcagtg    3720
ctgccataac catgagtgat aacactgcgg ccaacttact tctgacaacg atcggaggac    3780
cgaaggagct aaccgctttt ttgcacaaca tgggggatca tgtaactcgc cttgatcgtt    3840
gggaaccgga gctgaatgaa gccataccaa acgacgagcg tgacaccacg atgcctgtag    3900
caatggcaac aacgttgcgc aaactattaa ctggcgaact acttactcta gcttcccggc    3960
aacaattaat agactggatg gaggcggata agttgcagg accacttctg cgctcggccc     4020
ttccggctgg ctggtttatt gctgataaat ctggagccgg tgagcgtggg tctcgcggta    4080
tcattgcagc actggggcca gatggtaagc cctcccgtat cgtagttatc tacacgacgg    4140
ggagtcaggc aactatggat gaacgaaata gacagatcgc tgagataggt gcctcactga    4200
ttaagcattg gtaactgtca gaccaagttt actcatatat actttagatt gatttaaaac    4260
ttcattttta atttaaaagg atctaggtga agatccttt tgataatctc atgaccaaaa     4320
tcccttaacg tgagttttcg ttccactgag cgtcagaccc cgtagaaaag atcaaaggat    4380
cttcttgaga tccttttttt ctgcgcgtaa tctgctgctt gcaaacaaaa aaaccaccgc    4440
taccagcggt ggtttgtttg ccggatcaag agctaccaac tcttttccg aaggtaactg     4500 gcttcagcag agcgcagata ccaaatactg tccttctagt gtagccgtag ttaggccacc    4560
acttcaagaa ctctgtagca ccgcctacat acctcgctct gctaatcctg ttaccagtgg    4620
ctgctgccag tggcgataag tcgtgtctta ccgggttgga ctcaagacga tagttaccgg    4680
ataaggcgca gcggtcgggc tgaacggggg gttcgtgcac acagcccagc ttggagcgaa    4740
cgacctacac cgaactgaga tacctacagc gtgagctatg agaaagcgcc acgcttcccg    4800
aagggagaaa ggcggacagg tatccggtaa gcggcagggt cggaacagga gagcgcacga    4860
gggagcttcc agggggaaac gcctggtatc tttatagtcc tgtcgggttt cgccacctct    4920
gacttgagcg tcgatttttg tgatgctcgt caggggggcg gagcctatgg aaaaacgcca    4980
gcaacgcggc ctttttacgg ttcctggcct tttgctggcc ttttgctcac atgttctttc    5040
ctgcgttatc ccctgattct gtggataacc gtattaccgc ctttgagtga gctgataccg    5100
ctcgccgcag ccgaacgacc gagcgcagcg agtcagtgag cgaggaagcg gaaga         5155
```

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic -continued

```
      primer

<400> SEQUENCE: 7
gaatctgtta gttagttact tggat                                           25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgattatagc tattatcaca gactc                                           25
```